US010363288B2

(12) United States Patent
Michels et al.

(10) Patent No.: US 10,363,288 B2
(45) Date of Patent: Jul. 30, 2019

(54) INSULIN MIMOTOPES AND METHODS OF USING THE SAME

(71) Applicants: THE REGENTS OF THE UNIVERSITY OF COLORADO, a body corporate, Denver, CO (US); NATIONAL JEWISH HEALTH, Denver, CO (US)

(72) Inventors: Aaron Michels, Aurora, CO (US); John Kappler, Denver, CO (US); Peter A. Gottlieb, Englewood, CO (US)

(73) Assignees: National Jewish Health, Denver, CO (US); The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 15/541,074

(22) PCT Filed: Jan. 13, 2016

(86) PCT No.: PCT/US2016/013252
§ 371 (c)(1),
(2) Date: Jun. 30, 2017

(87) PCT Pub. No.: WO2016/115253
PCT Pub. Date: Jul. 21, 2016

(65) Prior Publication Data
US 2018/0117124 A1    May 3, 2018

Related U.S. Application Data

(60) Provisional application No. 62/103,429, filed on Jan. 14, 2015.

(51) Int. Cl.
*G01N 33/50* (2006.01)
*A61K 38/28* (2006.01)
*C07K 14/62* (2006.01)

(52) U.S. Cl.
CPC .............. *A61K 38/28* (2013.01); *C07K 14/62* (2013.01); *G01N 33/5091* (2013.01); *G01N 2333/5428* (2013.01); *G01N 2333/57* (2013.01); *G01N 2800/042* (2013.01)

(58) Field of Classification Search
None
See application file for complete search history.

(56) References Cited

U.S. PATENT DOCUMENTS

| | | |
|---|---|---|
| 4,207,890 A | 6/1980 | Mamajek et al. |
| 4,434,153 A | 2/1984 | Urquhart et al. |
| 4,691,018 A | 9/1987 | Mori et al. |
| 4,735,804 A | 4/1988 | Caldwell et al. |
| 4,758,436 A | 7/1988 | Caldwell et al. |
| 4,767,627 A | 8/1988 | Caldwell et al. |
| 4,783,337 A | 11/1988 | Wong et al. |
| 5,415,994 A | 5/1995 | Imrich et al. |
| 5,424,193 A | 6/1995 | Pronovost et al. |
| 5,475,033 A | 12/1995 | Ohmori et al. |
| 5,594,100 A | 1/1997 | Wegman |
| 5,780,057 A | 7/1998 | Conte et al. |
| 5,939,281 A | 8/1999 | Lehmann et al. |
| 6,001,567 A | 12/1999 | Brow et al. |
| 6,207,197 B1 | 3/2001 | Illum et al. |
| 6,218,132 B1 | 4/2001 | Spack et al. |
| 7,144,569 B1 | 12/2006 | Anderson et al. |
| 7,749,503 B2 | 7/2010 | Tobia et al. |
| 8,053,197 B2 | 11/2011 | Vandenbark et al. |
| 8,314,210 B2 | 11/2012 | Wucherpfennig et al. |
| 9,629,848 B2 | 4/2017 | Eisenbarth et al. |
| 9,820,957 B2 | 11/2017 | Orndorff et al. |
| 2002/0150914 A1 | 10/2002 | Andersen et al. |
| 2003/0190665 A1 | 10/2003 | Vandenbark |
| 2004/0096734 A1 | 5/2004 | Calundann et al. |
| 2004/0137514 A1 | 7/2004 | Steenbakkers |
| 2004/0253276 A1 | 12/2004 | Sato et al. |
| 2004/0265327 A1 | 12/2004 | Grassetti et al. |
| 2005/0222270 A1 | 10/2005 | Olney et al. |
| 2006/0183670 A1 | 8/2006 | Orban |
| 2007/0021341 A1 | 1/2007 | Sela et al. |
| 2007/0196369 A1 | 8/2007 | Hoogenboom et al. |
| 2008/0194462 A1 | 8/2008 | Wucherpfennig et al. |
| 2008/0214656 A1 | 9/2008 | Lim et al. |
| 2010/0172875 A1 | 7/2010 | Phan et al. |
| 2010/0172920 A1 | 7/2010 | Rottiers et al. |
| 2010/0233253 A1 | 9/2010 | Kavimandan et al. |
| 2011/0245334 A1 | 10/2011 | Du et al. |
| 2012/0171212 A1 | 7/2012 | Eisenbarth et al. |

(Continued)

FOREIGN PATENT DOCUMENTS

| | | |
|---|---|---|
| EP | 0098475 | 1/1984 |
| JP | S49-027860 | 7/1974 |

(Continued)

OTHER PUBLICATIONS

Daniel, Carolin et al, "Prevention of type 1 diabetes in mice by tolerogenic vaccination wiht a strong agonist insulin nninnetope." J. Exp. Med. (2011) 208(7) p. 1501-1510.*

(Continued)

*Primary Examiner* — Fred H Reynolds
(74) *Attorney, Agent, or Firm* — Stanek Lemon Crouse & Meeks, PA

(57) ABSTRACT

Methods for inhibiting an autoimmune disease by administering to a subject a therapeutically effective amount of a composition that induces conversion of naive T cells into Foxp3+ regulatory T cells to induce immunosuppression in the subject. Methods for detecting in a subject an autoimmune disease or a predisposition to an autoimmune disease, and methods for assessing the efficacy of a therapy for an autoimmune disease, particularly type 1 diabetes.

5 Claims, 9 Drawing Sheets
Specification includes a Sequence Listing.

(56) References Cited

U.S. PATENT DOCUMENTS

| | | | |
|---|---|---|---|
| 2012/0195929 | A1 | 8/2012 | Eisenbarth et al. |
| 2013/0017262 | A1 | 1/2013 | Mullen et al. |
| 2013/0115188 | A1 | 5/2013 | Fritsche et al. |
| 2014/0050807 | A1 | 2/2014 | Leighton |
| 2015/0010631 | A1 | 1/2015 | Getts |

FOREIGN PATENT DOCUMENTS

| | | |
|---|---|---|
| JP | H09-52847 | 2/1997 |
| WO | WO 84/02843 | 8/1984 |
| WO | WO 94/01775 | 1/1994 |
| WO | WO 94/29696 | 12/1994 |
| WO | WO 99/67641 | 12/1999 |
| WO | WO 00/38650 | 7/2000 |
| WO | WO 00/39587 | 7/2000 |
| WO | WO 01/64183 | 9/2001 |
| WO | WO 03/070752 | 8/2003 |
| WO | WO 2004/007528 | 1/2004 |
| WO | WO 2004/110373 | 12/2004 |
| WO | WO 2005/085323 | 9/2005 |
| WO | WO 2010/141883 | 12/2010 |
| WO | WO 2012/162697 | 11/2012 |
| WO | WO 2016/191634 | 12/2016 |

OTHER PUBLICATIONS

The ProImmune web page describing Elispot assays, https://proimmune.com/ecommerce/page.php?page=elispot, available online Nov. 2013.*

Maindonald, John, "Experimental Design." https://web.archive.org/web/20130411093944/https://maths-people.anu.edu.au/~johnm/planning/expdes.pdf, available online Apr. 2013.*

Kmieciak, Maciej et al, "Human t cells express cd25 and foxp3 upon activation and exhibit effector/memory phenotypes without any regulatory/suppressor function." J. Trans. Med. (2009) 7:89.*

U.S. Appl. No. 14/341,767, filed, Jul. 26, 2014, Eisenbarth et al.
U.S. Appl. No. 15/355,738, filed Nov. 18, 2016, Eisenbarth et al.
U.S. Appl. No. 15/495,132, filed Apr. 24, 2017, Eisenbarth et al.
U.S. Appl. No. 15/556,710, filed Sep. 8, 2017, Anchordoquy et al.
U.S. Appl. No. 15/817,739, filed Nov. 30, 2017, Orndorff et al.

Aharoni et al., "Immunomodulation of experimental allergic encephalomyelitis by antibodies to the antigen-la complex," Nature, 1991, vol. 351, pp. 147-150.

ALDOMET® (Methyldopa), Merck & Co., Inc., Product Label, (NDA 13-400/S-086, 2004, pp. 3-8.

Ames et al., "Stereochemical Course In Vivo of Alpha-Methyldopa Decasrboxylation in Rat Brains," Biochem. Pharmacology, 1977, vol. 26(19), pp. 1757-1762.

Aoki et al., "NOD mice and autoimmunity," Autoimmun. Rev., 2005, vol. 4, pp. 373-379.

Au et al., "The Metabolism of 14C-Labelled 1-Methyldopa in Normal and Hypertensive Human Subjects," Biochem. J., 1972, vol. 129, pp. 1-10.

Auclair et al., "Comparative pharmacokinetics of D- and L-alphamethyldopa in plasma, aqueous humor, and cerebrospinal fluid in rabbits," Fundamental & Clinical Pharmacology, 1988, vol. 2(4), pp. 283-293.

Badiola et al. "Enantioselective Construction of Tetrasubstituted Stereogenic Carbons through Brønsted Base Catalyzed Michael Reactions: α'-Hydroxy Enones as Key Enoate Equivalent," Journal of the American Chemical Society, Dec. 2014, vol. 136, No. 51, pp. 17869-17881 (Abstract Only).

Boulard et al., "An interval tightly linked to but distinct from the h2 complex controls both overt diabetes (iddl6) and chronic experimental autoimmune thyroiditis (ceatl) in nonobese diabetic mice," Diabetes, 2002, vol. 51, pp. 2141-2147.

Bresson et al., "Moving towards efficient therapies in type 1 diabetes: To combine or not to combine?," Autoimmun Rev, 2007, vol. 6(5), pp. 315-322, 11 pages.

Chung et al., "Competitive Inhibition In Vivo and Skewing of the T Cell Repertoire of Antigen-Specific CTL Priming by an Anti-Peptide-MHC Monoclonal Antibody," J. Immunol., 2001, vol. 167, pp. 699-707.

Cochlovius et al., "In Vitro and In Vivo Induction of a Th Cell Response Toward Peptides of the Melanoma-Associated Glycoprotein 100 Protein Selected by the TEPITOPE Program," J. Immunol., 2000, vol. 165, pp. 4731-4741.

Corper et al., "A structural framework for deciphering the link between I-Ag7 and autoimmune diabetes," Science, 2000, vol. 288, pp. 505-511.

Crawford et al., "Mimotopes for Alloreactive and Conventional T Cells in a Peptide-MHC Display Library," PLoS. Biol., 2004, vol. 2, p. 0523-0533.

Crawford et al., "Specificity and detection of insulin-reactive CDR+ T Cells in Type 1 diabetes in the nonobese diabetic (NOD) mouse," PNAS, 2011, vol. 108(40), pp. 16729-16734.

Czerkinsky et al., "Reverse ELISPOT assay for clonal analysis of cytokine production. I. Enumeration of gamma-interferon-secreting cells," Journal of Immunological Methods, 1988, vol. 110(1), pp. 29-36.

Daniel et al., "Prevention of type 1 diabetes in mice by tolerogenic vaccination with a strong agonist insulin mimetope," The Journal of Experimental Medicine, 2011, vol. 208(7), pp. 1501-1510.

Demuth et al., "Vaccine delivery with microneedle skin patches in nonhuman primates," Nat. Biotechnol. 2013, vol. 31(12), pp. 1082-1085.

Faideau et al., "Expression of preproinsulin-2 gene shapes the immune response to preproinsulin in normal mice," J. Immunol., 2004, vol. 172, pp. 25-33.

Fairbrother et al., "Effects of Three Plant Growth Regulators on the Immune Response of Young and Aged Deer Mice Peromyscus Maniculatus," Arch. Environ. Contam, Toxicol., 1986, vol. 15, pp. 265-275.

Fife et al., "Insulin-induced remission in new-onset NOD mice is maintained by the PD-1-PD-L1 pathway," J. Experimental Med., 2006, vol. 203, pp. 2737-2747.

Fontenot et al., "Foxp3 programs the development and function of CD4+CD25+ regulatory T cells," Nature Immunology, 2003, vol. 4, pp. 330-336.

Fujisawa et al., "MHC-linked susceptibility to type 1 diabetes in the NOD mouse: further localization of ldd16 by subcongenic analysis," Ann. NY Acad. Sci., 2006, vol. 1079, pp. 118-121.

Fukushima et al., "Combined insulin B:9-23 self-peptide and polyinosinic-polycytidylic acid accelerate insulitis but inhibit development of diabetes by increasing the proportion of CD4+Foxp3+ regulatory T cells in the islets in non-obese diabetic mice," Biochemical and Biophysical Research Communications, 2008, vol. 367, pp. 719-724.

Grigoriadis et al., "Alpha-Methyldopa-Induced Autoimmune Hemolytic Anemia in the Third Trimester of Pregnancy," Case Reports in Obstetrics and Gynecology, 2013, 2 pages, 2013:150278.

Hattori et al., "The NOD mouse: recessive diabetogenic gene within the major histocompatibility complex," Science, 1986, vol. 231, pp. 733-735.

Homann et al., "An immunologic homunculus for type 1 diabetes," J. Clin. Invest., 2006, vol. 116, pp. 1212-1215.

Hovhannisyan et al., "The role of HLA-DQ8 beta57 polymorphism in the anti-gluten T-cell response in coeliac disease," Nature, 2008, vol. 456, pp. 534-538.

Hurtenback, "Prevention of Autoimmune Diabetes in Non-Obese Diabetic Mice by Treatment with a Class II Major Histocompatibility Complex-blocking Peptide," Journal of Experimental Medicine, 1993, vol. 177(5), pp. 1499-1504.

Itoh et al., "Thymus and Autoimmunity: Production of CD25+ CD4+ Naturally Anergic and Suppressive T Cells as a Key Function of the Thymus in Maintaining Immunologic Self-Tolerance," J. Immnol. 1999, vol. 162, pp. 5317-5326.

Jasinski et al., "Transgenic Insulin (B:9-23) T-Cell Receptor Mice Develop Autoimmune Diabetes Dependent Upon RAG Genotype, H-2g7 Homozygosity, and Insulin 2 Gene Knockout," Diabetes, 2006, vol. 55, pp. 1978-1984.

(56) References Cited

OTHER PUBLICATIONS

Kachapati et al., "The Non-Obese Diabetic (NOD) Mouse as a Model of Human Type 1 Diabetes." Animal Models in Diabetes Research. Methods in Molecular Biology, 2012, vol. 933, pp. 3-16.
Kanagawa et al., "The role of I-Ag7 β chain in peptide binding and antigen recognition by T cells," Int Immunol., 1998, vol. 9, pp. 1523-1526.
Kobayashi et al., "Conserved T cell receptor alpha-chain induces insulin autoantibodies," Proc. Natl. Acad. Sci. USA., 2008, vol. 105, pp. 10090-10094.
Lee et al., "Structure of a human insulin peptide-HLA-DQ8 complex and susceptibility to type 1 diabetes." Nature Immunology, 2001, vol. 2(6), pp. 501-507.
Levisetti et al., "The Insulin-Specific T Cells of Nonobese Diabetic Mice Recognize a Weak MHC-Binding Segment in More Than One Form," Journal of Immunology, 2007, vol. 178(10), pp. 6051-6057.
Levisetti et al., "Weak proinsulin peptide-major histocompatibility complexes are targeted in autoimmune diabetes in mice," Diabetes, 2008, vol. 57, pp. 1852-1860.
Li et al., A computer screening approach to immunoglobulin superfamily structures and interactions: Discovery of small non-peptidic CD4 inhibitors as novel immunotherapeutics, Proc. Natl. Acad. Sci. USA, 1997, vol. 94, pp. 73-78.
Mareeva et al., "Antibody Specific for the Peptide-Major Histocompatibility Complex," J. Biol. Chem., 2004, vol. 279(43), pp. 44243-44249.
Masteller et al., "Peptide-MHC Class II Dimers as Therapeutics to Modulate Antige-Specific T Cell Responses in Autoimmune Diabetes," J. Immunol., 2003, vol. 171, pp. 5587-5595.
Merfeld et al., "The effect of pH and concentration on alpha-methyldopa absorption in man," J Pharm Pharmacol., 1986, vol. 38, pp. 815-822.
Metrano et al. "Peptide-Catalyzed Conversion of Racemic Oxazol-5(4H)-ones into Enantiomerically Enriched α-Amino Acid Derivatives," The Journal of Organic Chemistry, Feb. 2014, vol. 79, No. 4, pp. 1542-1554.
Mordes et al., "Rat Models of Type 1 Diabetes: Genetics, Environment, and Autoimmunity," ILAR Journal, 2004, vol. 45, No. 3, pp. 278-291.
Moriyama et al., "Evidence for a primary islet autoantigen (preproinsulin 1) for insulitis and diabetes in the nonobese diabetic mouse," Proc. Natl Acad. Sci. USA, 2003, vol. 100, pp. 10376-10381.
Moseman et al., "Human Plasmacytoid Dendritic Cells Activated by CpG Oligodeoxynucleotides Induce the Generation of CD4+CD25+ Regulatory T Cells," The Journal of Immunology. 2004, vol. 173, pp. 4433-4442.
Nakayama et al., "Prime role for an insulin epitope in the development of type 1 diabetes in NOD mice," Nature, 2005, vol. 435(7039), pp. 220-223, author manuscript, 10 pages.
Nakayama et al., "Priming and effector dependence on insulin B:9-23 peptide in NOD islet autoimmunity," J. Clin. Invest., 2007, vol. 117, pp. 1835-1843.
Nakayama et al., "Regulatory vs. inflammatory cytokine T-cell responses to mutated insulin peptides in healthy and type 1 diabetic subjects," PNAS, 2015, vol. 112(14), pp. 4429-4434.
Oikonmakos et al., "Allosteric inhibition of glycogen phosphorylase alpha by the potential antidiabetic drug 3-isopropyl 4-(2-chorophenyl)-1,4-dihydro-1-ethyl-2-methyl-pyridine-3,5,6-tricarboxylate," Protein Science, 1999, vol. 8, pp. 1930-1945.
Orban et al., "Autoantigen-specific regulatory T Cells induced in patients with Type 1 Diabetes Mellitus by Insulin B-chain immunotherapy," Journal of Autoimmunity, 2010, vol. 34(4), pp. 408-415, 21 pages.
Pietropaolo et al., "Primer: Immunity and Autoimmunity," Diabetes, 2008, vol. 57, pp. 2872-2882.
Puri et al., "Modulation of the Immune Response in Multiple Sclerosis," J. Immunol., 1997, vol. 158, pp. 2471-2476.
Renwick et al., "The Absorption and Conjugation of Methyldopa in Patients with Celiac and Crohn's Diseases During Treatment," Br. J. Clin. Pharmac., 1983, vol. 16, pp. 77-83.
Rosenblum et al., "Treating Human Autoimmunity: Current Practice and Future Prospects," Sci Transl Med, 2012, 4(125), 125sr1, pp. 1-20.
Sakaguchi et al., "Immunologic self-tolerance maintained by activated T cells expressing IL-2 receptor alpha-chains (CD25), Breakdown of a single mechanism of self-tolerance causes various autoimmune diseases," The Journal of Immunology, 1995, vol. 155(3), pp. 1151-1164c.
Salvati et al., "Recombinant human interleukin 10 suppresses gliadin dependent T cell activation in ex vivo cultured coeliac intestinal mucosa," Gut, 2005, retrieved from gut.bmj.com, retrieved on Aug. 21, 2012, vol. 54, pp. 46-53.
Savoie et al., "Use of BONSAI decision trees for the identification of potential MHC class I peptide epitope motifs," Pacific Symposium on Biocomputing, 1999, vol. 4, pp. 182-189, 8 pages.
Scheen, "Pathophysiology of type 2 diabetes," Acta Clinica Belgica, 2003, vol. 58(6), pp. 335-341.
Sharma et al. "Gastroretentive Drug Delivery System: An Approach to Enhance Gastric Retention for Prolonged Drug Release," International Journal of Pharmaceutical Sciences and Research, 2014, vol. 5(4), pp. 1095-1106.
Sjoerdsma et al., "Studies on the Metabolism and Mechanism of Action of Methyldopa," Circulation, 1963, vol. 28, pp. 492-502.
Sosinowski et al., "Type 1 diabetes: primary antigen/peptide/register/trimolecular complex," Immunologic Research, 2013, vol. 55, pp. 270-276.
Stadinski et al., "Diabetogenic T cells recognize insulin bound to IAg7 in an unexpected, weakly binding register," PNAS, 2010, vol. 107(24), pp. 10978-10983.
Stern et al., "Action of α-methyldopa on the intention tremor," Arzneinittel-Forschung, 1970, vol. 20(5), pp. 727-728.
Suri et al, "Natural peptides selected by diabetogenic DQ8 and murine I-A g7 molecules show common sequence specificity," The Journal of Clinical Investigation, 2005, vol. 115(8), pp. 2268-2276.
Suri et al., "The Murine Diabetogenic Class II Histocompatibility Molecule I-A (g7): Structural and Functional Properties and Specificity of Peptide Selection," Adv. Immunol., 2005, vol. 88, pp. 235-265.
Suri-Payer et al., "CD4+CD25+ T Cells Inhibit Both the Induction and Effector Function of Autoreactive T Cells and Represent a Unique Lineage of Immunoregulatory Cells" The Journal of Immunology, 1998, vol. 160, pp. 1212-1218.
Thomson et al., "FK 506: a novel immunosuppressant for treatment of autoimmune disease: Rationale and preliminary clinical experience," Springer Semin Immunopathol. 1993, vol. 14(4), 31 pages.
Todd et al., "A molecular basis for MHC class II associated autoimmunity," Science, 1988, vol. 240, pp. 1003-1009.
Vandenbark et al., "Treatment of multiple sclerosis with T-cell receptor peptides: Results of a double-blind pilot trial," Nature Medicine, 1996, vol. 2, pp. 1109-1115.
Wallis et al., "Type 1 Diabetes in the BB rat: A polygenic disease," Diabetes, 2009, vol. 58(4), pp. 1007-1017.
Wang et al., "Immunopharmacological and antitumor effects of second-generation immunomodulatory oligonucleotides containing synthetic CpR motifs," International Journal of Oncology, 2004, vol. 24, pp. 901-908.
Wicker et al., "Type 1 diabetes genes and pathways shared by humans and NOD mice," J. Autoimmun., 2005, vol. 25 (Suppl), pp. 29-33.
Wucherpfennig, "Insights into autoimmunity gained from structural analysis of MHC-peptide complexes," Current Opinion in Immunology, 2001, vol. 13, pp. 650-656.
Zhang et al., "Immunization with an insulin peptide-MHC complex to prevent type 1 diabetes of NOD mice," Diabetes Meta Res Rev, 2011, vol. 27, pp. 784-789.
Zhong et al., "Production, specificity, and functionality of monoclonal antibodies to specific peptide-major histocompatibility complex class II complexes formed by processing of exogenous protein," Proc. Natl. Acad. Sci. USA, 1997, vol. 94, pp. 13856-13861.
International Search Report and Written Opinion for International (PCT) Application No. PCT/US2016/013252, dated Mar. 30, 2016, 11 pages.

(56) References Cited

OTHER PUBLICATIONS

International Patentability Search Report for International (PCT) Application No. PCT/US2016/013252, dated Jul. 27, 2017, 10 pages.
International Search Report and Written Opinion for International (PCT) Application No. PCT/US2017/23571, dated Jul. 3, 2017, 17 pages.
International Search Report and Written Opinion for International (PCT) Application No. PCT/US2012/039849, dated Sep. 21, 2012, 9 pages.
International Preliminary Report on Patentability for International (PCT) Application No. PCT/US2012/039849, dated Dec. 5, 2013, 7 pages.
International Search Report and Written Opinion for International (PCT) Application No. PCT/US2016/034527, dated Aug. 25, 2016, 13 pages.
International Preliminary Report on Patentability for International (PCT) Patent Application No. PCT/US2016/034527, dated Dec. 7, 2017 12 pages.
Official Action for U.S. Appl. No. 15/466,026, dated May 17, 2017 24 pages.
Notice of Allowance for U.S. Appl. No. 15/466,026, dated Oct. 13, 2017 8 pages.
Official Action for U.S. Appl. No. 15/894,118, dated May 14, 2018 8 pages, Retriction Requirement.
Official Action for U.S. Appl. No. 14/119,926, dated May 21, 2015 6 pages, Restriction Requirement.
Official Action for U.S. Appl. No. 14/119,926, dated Nov. 3, 2015 19 pages.
Notice of Allowance for U.S. Appl. No. 14/119,926, dated Jul. 26, 2016 7 pages.
Notice of Allowance for U.S. Appl. No. 14/119,926, dated Aug. 19, 2016 5 pages.
Official Action for U.S. Appl. No. 15/556,710, dated Mar. 29, 2018 11 pages, Restriction Requirement.
Leusch et al. "A short primer on benzene, toluene, ethylbenzene and xylenes (BTEX) in the environment and in hydraulic fracturing fluids," Griffith University, Nov. 17, 2010, 8 pages.
Official Action for Canada Patent Application No. 2,980,940, dated Jul. 9, 2018 4 pages.
Official Action for U.S. Appl. No. 15/894,118, dated Aug. 2, 2018 18 pages.
Notice of Allowance for U.S. Appl. No. 15/894,118, dated Dec. 6, 2018 10 pages.
Official Action for U.S. Appl. No. 15/556,710, dated Oct. 3, 2018 18 pages.
Extended European Search Report for European Patent Application No. 16737819.9, dated Mar. 1, 2019, 7 pages.
Extended European Search Report for European Patent Application No. 16800769.8, dated Jan. 8, 2019, 16 pages.

* cited by examiner

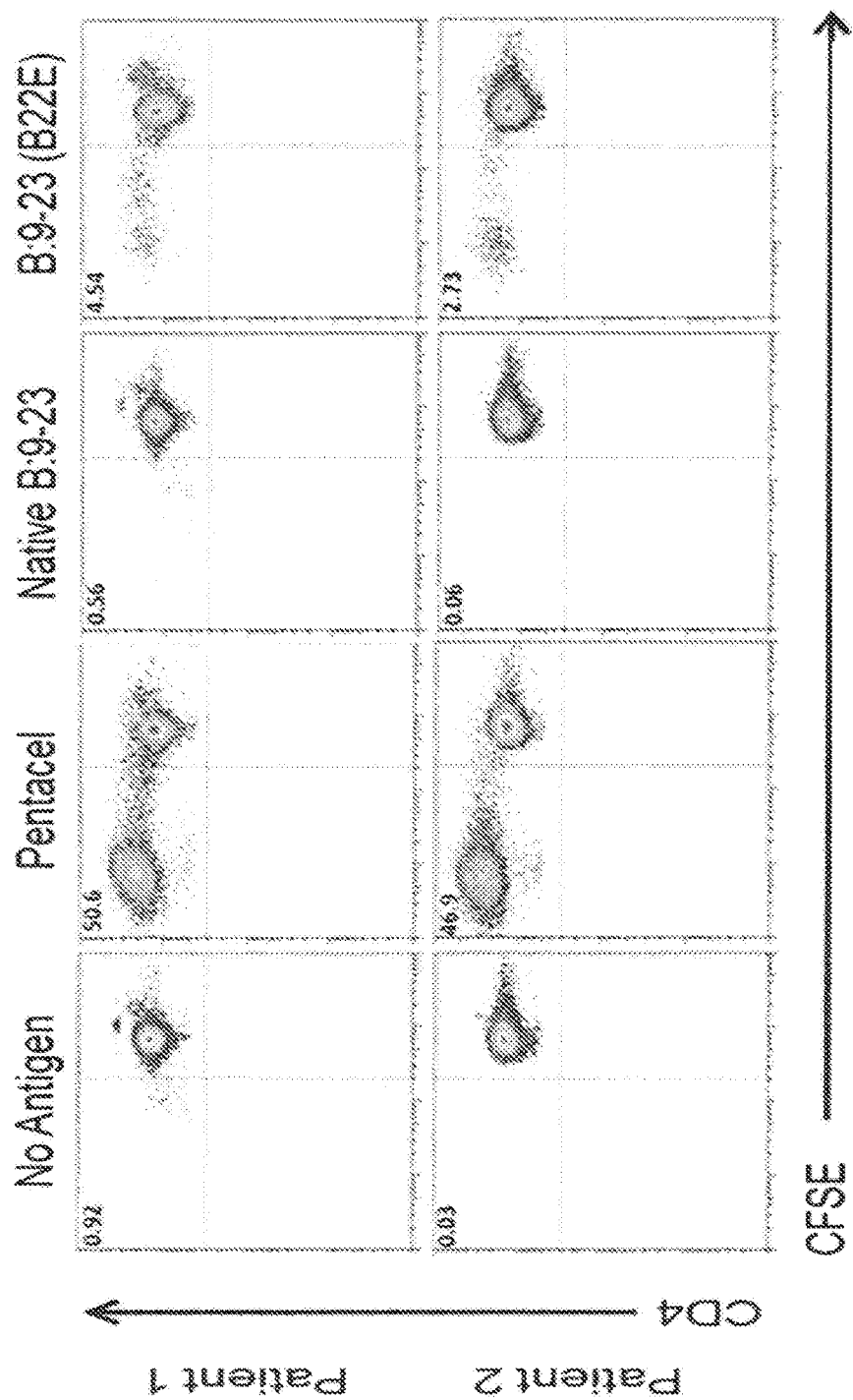

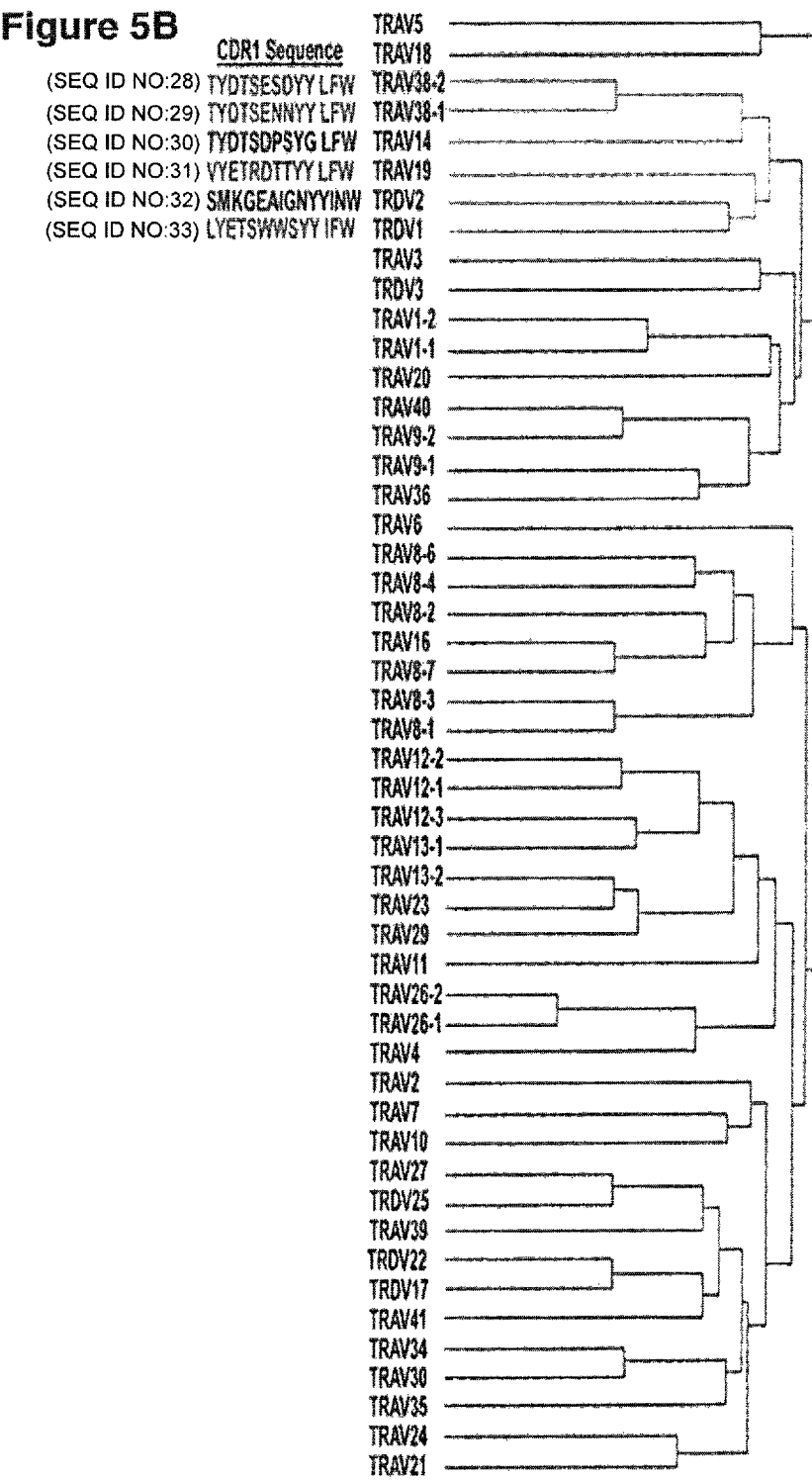

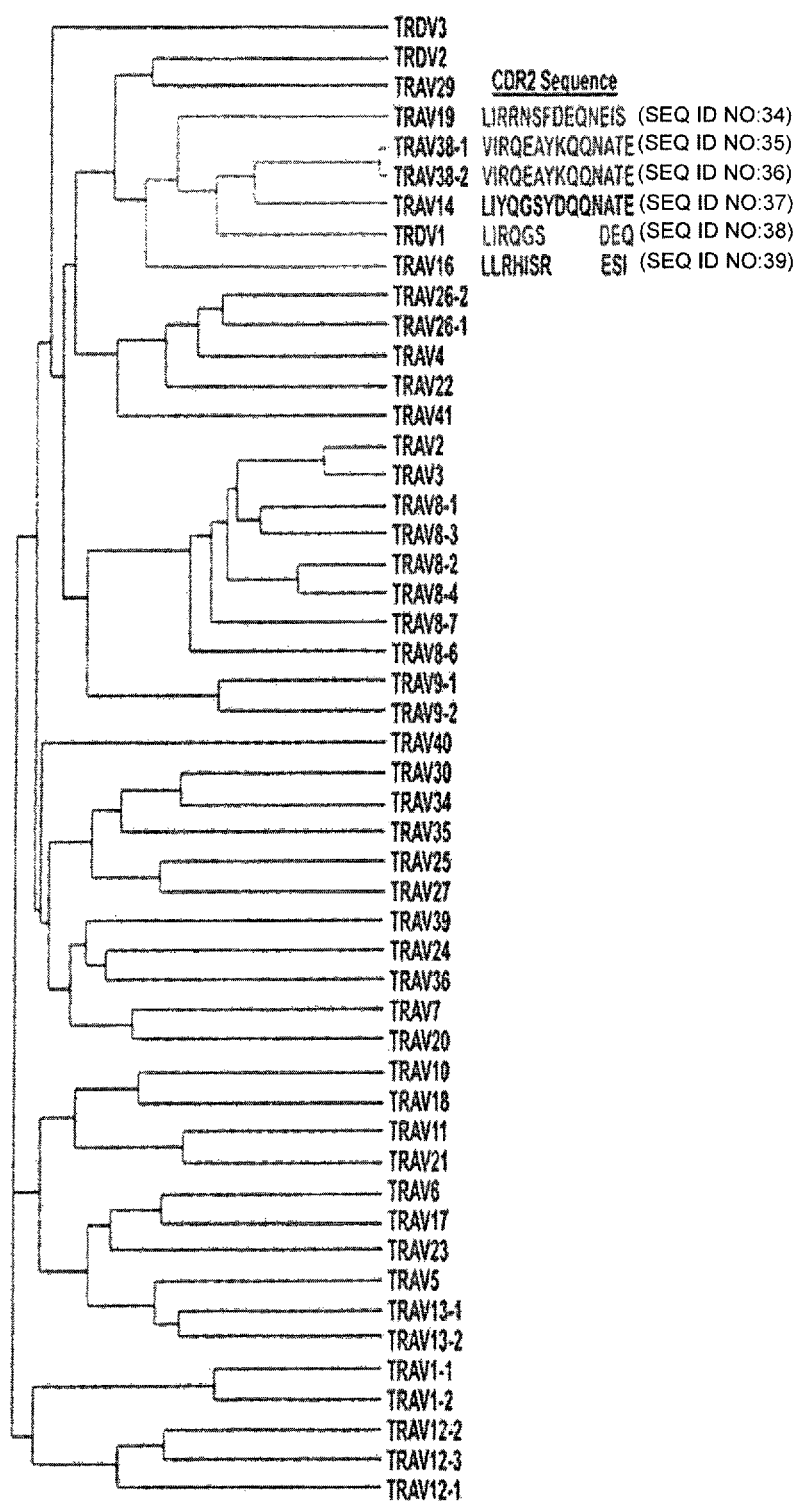

INSULIN MIMOTOPES AND METHODS OF USING THE SAME

CROSS REFERENCE TO RELATED APPLICATION

This application is a national stage application under 35 U.S.C. 371 of PCT Application No. PCT/US2016/013252, having an international filing date of Jan. 13, 2016, which designated the United States, which PCT application claimed the benefit of U.S. Application Ser. No. 62/103,429, filed on Jan. 14, 2015, both of which are incorporated herein by reference in their entirety.

GOVERNMENT INTEREST

This invention was made with Government support under grant numbers R01 DK032083 and K08 DK095995 awarded by the National Institute of Diabetes and Digestive Kidney Diseases. The U.S. Government has certain rights in the invention.

REFERENCE TO SEQUENCE LISTING

This application contains a Sequence Listing submitted as an electronic text file named "2848-166-PUS_Sequence_Listing_ST25.txt", having a size in bytes of 9000 bytes, and created on Feb. 28, 2019. The information contained in this electronic file is hereby incorporated by reference in its entirety pursuant to 37 CFR § 1.52(e)(5).

TECHNICAL FIELD

The invention relates to the field of autoimmune disorders, specifically to the monitoring and treatment of diabetes.

BACKGROUND

Type 1 diabetes (T1D), the autoimmune form of diabetes, results from T cell mediated destruction of insulin producing beta cells within pancreatic islets (1). The disease is dramatically increasing in incidence, doubling in the last two decades, and is predictable by the measurement of antibodies directed against proteins in beta cells (2-4). Despite being predictable, T1D onset cannot be delayed or prevented. Major efforts at disease prevention have been undertaken using preparations of insulin (subcutaneous, oral, and intranasal) to induce tolerance and delay the onset of clinical symptoms (5-7). Measuring insulin-specific T cell responses from the peripheral blood has been a challenging feat, but would allow for assessment of therapeutic response (e.g. converting an inflammatory T cell response (Th1) into a regulatory response), which has been a major obstacle in these trials.

Thus, there exists a need for improved methods of identifying and monitoring T1D-associated T cell responses in individuals, to select and administer individualized therapies to prevent or treat the disease and to efficiently and effectively monitor T1D disease progression after therapies are administered.

SUMMARY

Insulin is a major self-antigen for both T and B cells in murine and human T1D with insulin B chain amino acids 9-23 (B:9-23), a key epitope presented by major histocompatibility (MHC) class II molecules to CD4 T cells targeting pancreatic beta cells (8-10). There is strong evidence from the nonobese diabetic (NOD) mouse model of spontaneous autoimmune diabetes that pathogenic CD4 T cells recognize insulin B:9-23 presented in an unfavorable binding position or 'register' by the NOD MHC class II molecule, $IA^{g7}$ (9, 11, 12). A unique polymorphism in the $IA^{g7}$ beta chain at position 57 (Asp->Ser) favors the binding of peptides that place an acidic amino at the p9 position of its peptide binding groove. The B22 Arg of B:9-23 is a very poor match for this pocket when the peptide is bound in the pathogenic register. The binding of the peptide in this register can be greatly enhanced by creating a mimotope with mutation of B22 Arg→Glu, which now places the highly favorable acidic Glu in the p9 pocket. This peptide mimotope stimulates B:9-23 specific CD4 T cells about 100-fold better than the wild type peptide and fluorescent $IA^{g7}$ tetramers made with the altered peptide detect CD4 T cells in the pancreas and pancreatic lymph nodes of prediabetic NOD mice (12). In addition, this mimotope, but not the wild type B:9-23 peptide, administered at low doses, is capable of inducing tolerance and completely preventing diabetes onset in the NOD mouse (13).

Similar to the NOD class II molecule, human MHC class II genes, termed human leukocyte antigen (HLA), explain more than 50% of the genetic risk for T1D (14). The HLA-DQ8 (DQB*03:02) and DQ2 (DQB*02:01 and DQB*02:02) alleles increase risk for disease development with approximately 90% of all T1D individuals having one or both alleles (14-16). Strikingly, the polymorphic HLA-DQ6 (DQB*06:02) allele provides dominant protection from diabetes development (14).

The inventors sought to detect peripheral T cell responses to insulin in new-onset T1D patients, longstanding T1D patients and non-diabetic controls utilizing novel, modified insulin B chain peptides. Because the beta chains of DQ2 and DQ8 also bear a unique polymorphism at position 57 that favors peptides with acidic amino acids at the p9 position of their binding grooves (17), the inventors hypothesized that diabetogenic insulin reactive CD4 T cells in T1D patients may also recognize B:9-23 bound to DQ2 or DQ8 in the unfavorable register. If so, the B:9-23 mimotope with the B22 Arg→Glu mutation might detect these T cells much better than the wild type peptide. Therefore, the inventors examined T cells in the peripheral blood of new-onset T1D individuals for their responses to the mimotope vs. wild type B:9-23 peptide, and found numerous new-onset T1D patients with a robust inflammatory IFN-γ response to the insulin B:9-23 mimotope, but not the wild type peptide (5). In contrast, control subjects without diabetes or islet autoantibodies produced a regulatory Interleukin-10 (IL10; also known as human cytokine synthesis inhibitory factor (CSIF)) response to the insulin mimotope only if a diabetes protective allele was present, suggesting the presence of T cell tolerance to insulin in these individuals. The T cell responses were DQ restricted in T1D subjects with established disease as proliferation of CD4 T cells to the insulin mimotope could be blocked by a DQ monoclonal antibody. Analysis of T cell receptor V gene usage in the proliferating cells demonstrates skewing and clustering of dominantly used V alpha genes based upon similarity in complementarity determining regions (CDRs).

Figure 1:
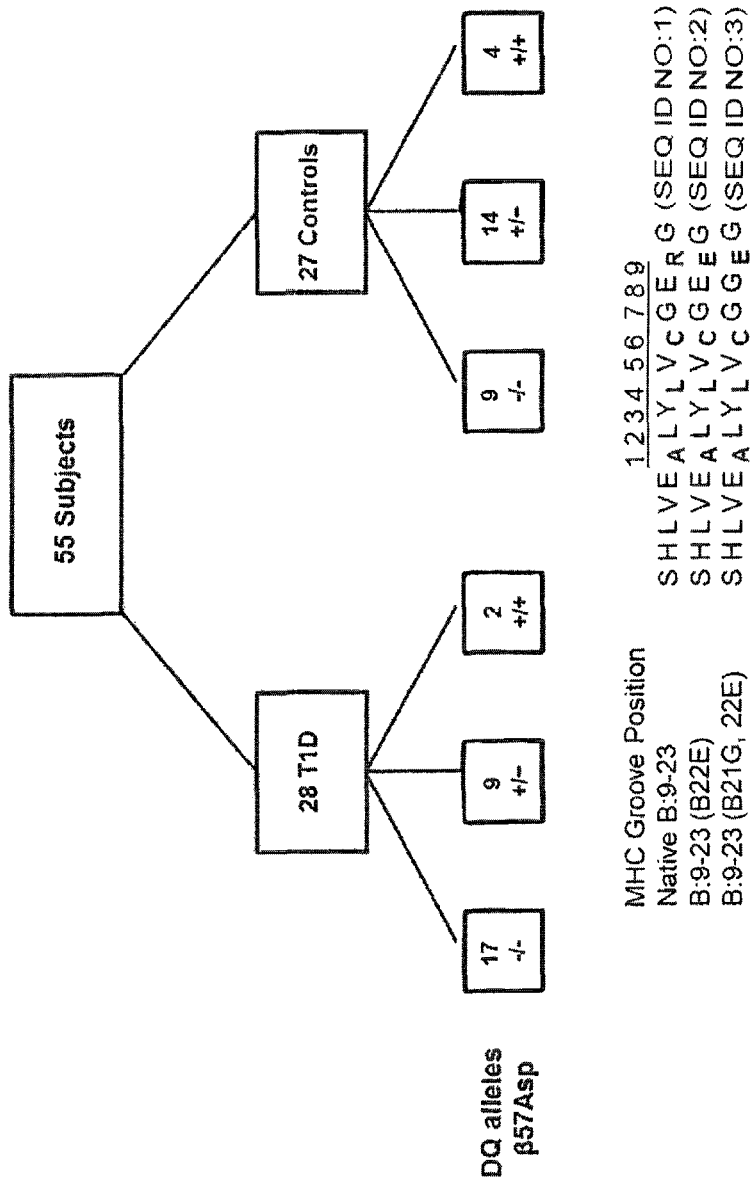
FIG. 1 shows a flowchart of the subjects and insulin peptides used for cytokine ELISPOT assays. The top of FIG.

1 shows a flowchart of the patients enrolled into the study with subgroups based upon disease and β57 aspartic acid-containing HLA-DQ alleles, and the bottom of FIG. 1 shows an amino acid sequence of the native insulin B:9-23 peptide and mimotopes and substitutions. The amino acids predicted to anchor each peptide to the DQ peptide binding groove in a low-affinity register of binding are shown in subscript. Thus, the B22 arginine is an unfavorable match for pocket 9 in the MHC groove. The two mimotopes shown in FIG. 1 have identical amino acid substitutions at position 8 and 9 to those which bind the NOD class II molecule, I-A$^{g7}$, and activate insulin specific T cells.

Figure 2:
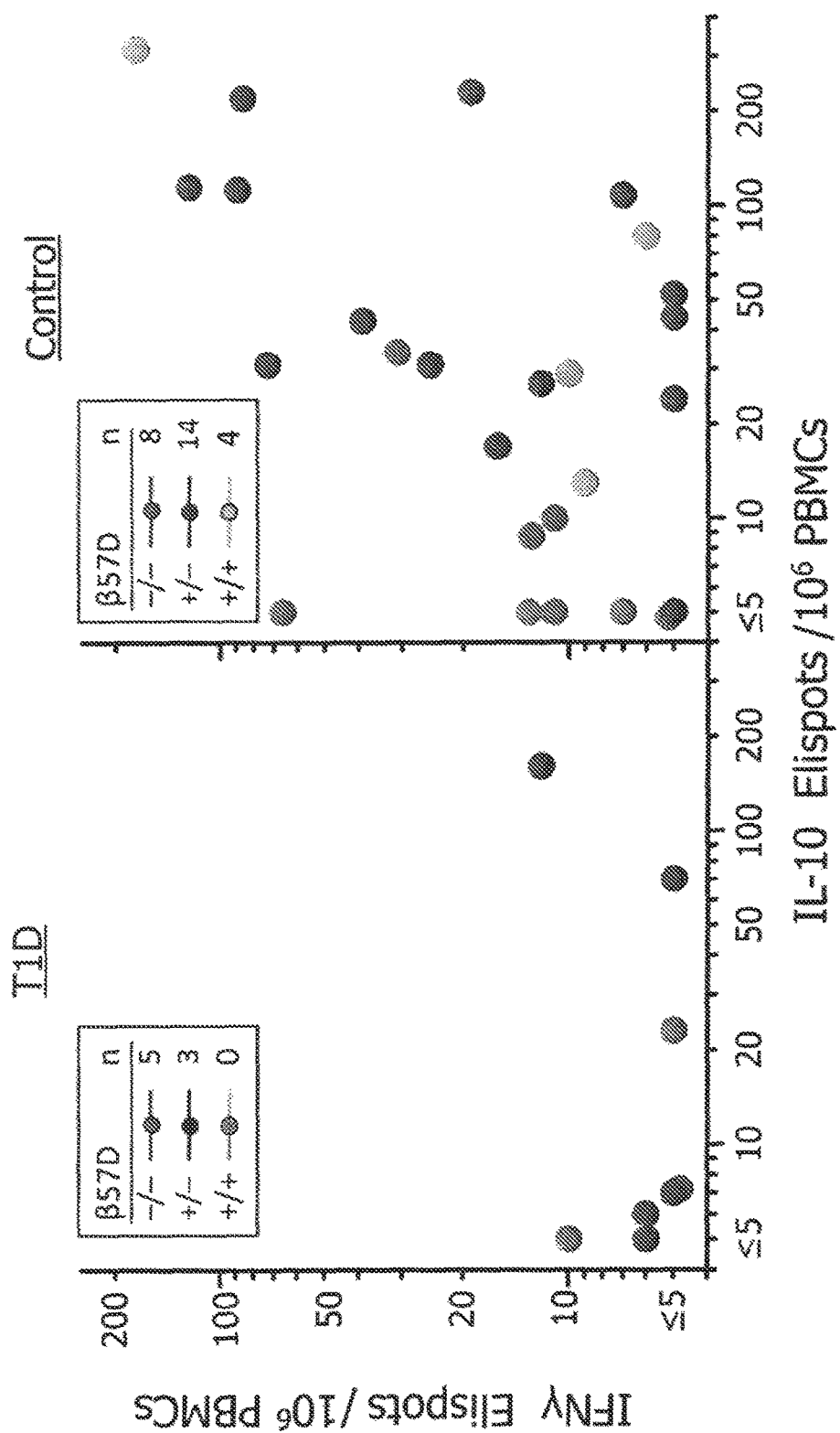

FIG. 2 is a comparison of IFN-γ to IL10 ELISPOT responses in T1D and control subjects to the insulin B:9-23 (B22E) mimotope. Each dot represents a single individual having both cytokines measured. Despite producing IFN-γ, controls make robust IL10 responses to the insulin mimotope. Controls with at least one β57Asp DQ allele (black and light grey circles) are IL10 responders, as 17/18 (94%) make more than 5 IL10 spots compared to 3/8 (38%) with no β57Asp DQ alleles (dark grey circles), p=0.005.

Figure 3:
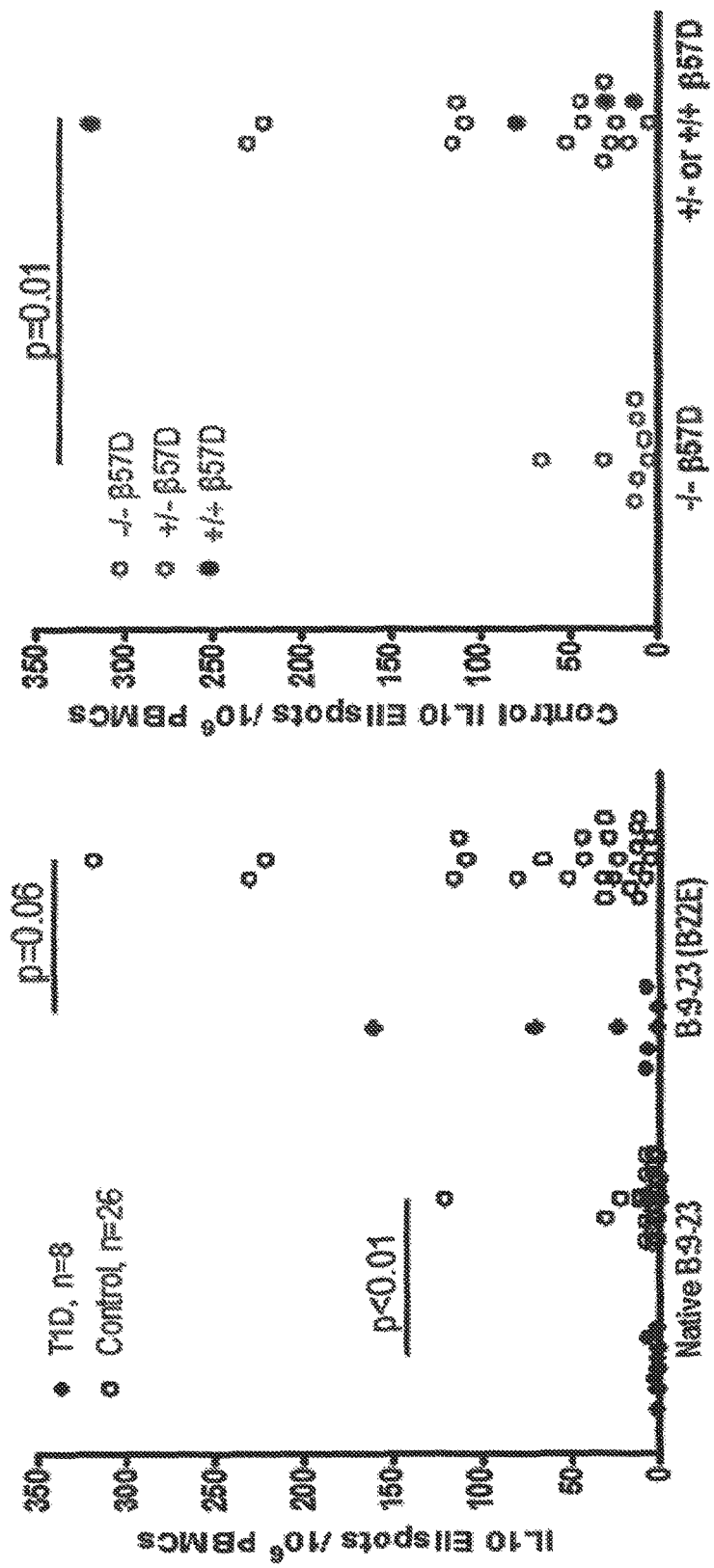

FIG. 3 shows IL10 ELISPOT responses in T1D and control subjects. As shown on the left, independent of DQ genotype, controls have a greater IL10 response to the native insulin B:9-23 peptide and a trend towards more with the insulin B22E mimotope compared to T1D. As shown on the right, by analyzing just control subjects, those with at one DQ allele (second column open circles) having the protective β57 aspartic acid polymorphism (n=18) produce greater IL10 responses to the insulin B22E mimotope than control subjects with two non-β57Asp DQ alleles (second column, solid circles) (n=9). Each dot represents the total number of IL10 ELISPOTs from 106 PBMCs for a single individual. The mean IL10 background response in the control subjects was 3.0 spots.

Figure 4B:
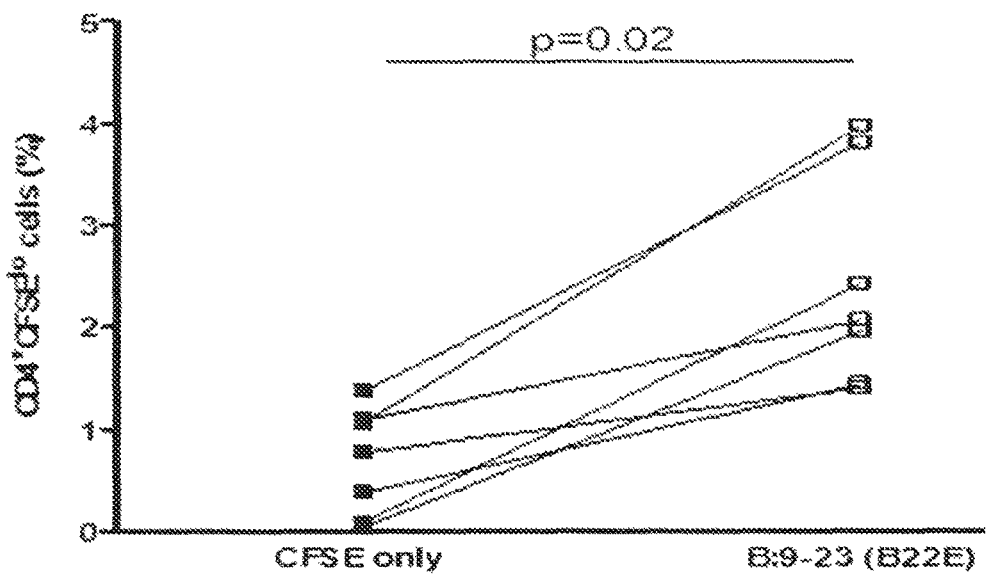
Figure 4C:
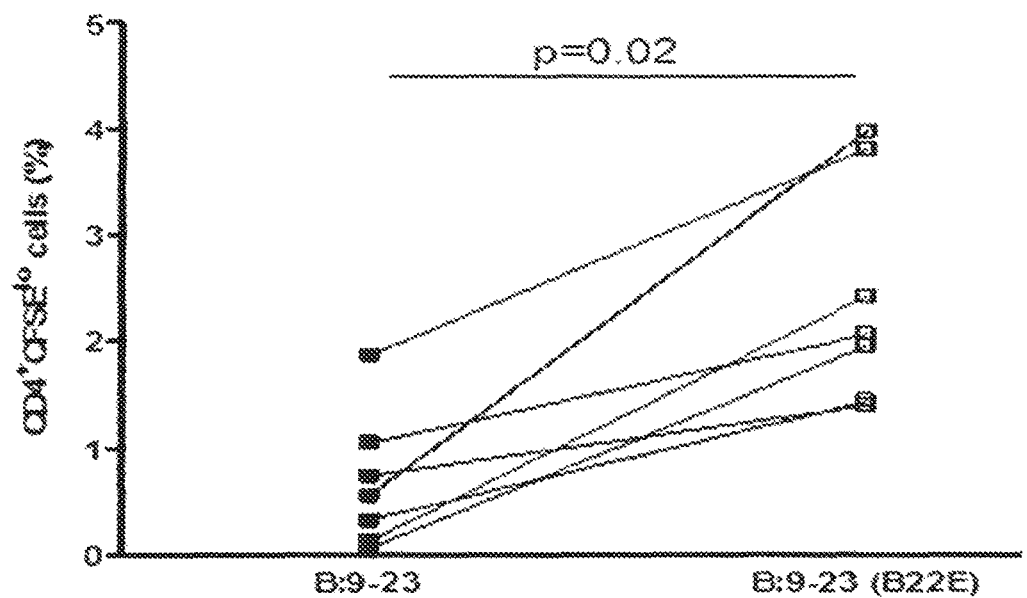
Figure 4D:
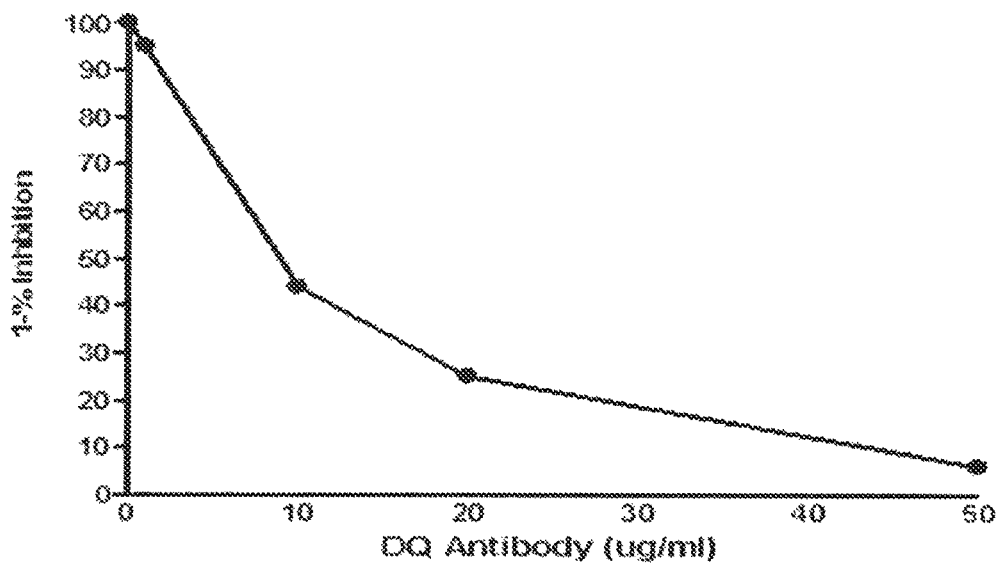
Figure 4E:
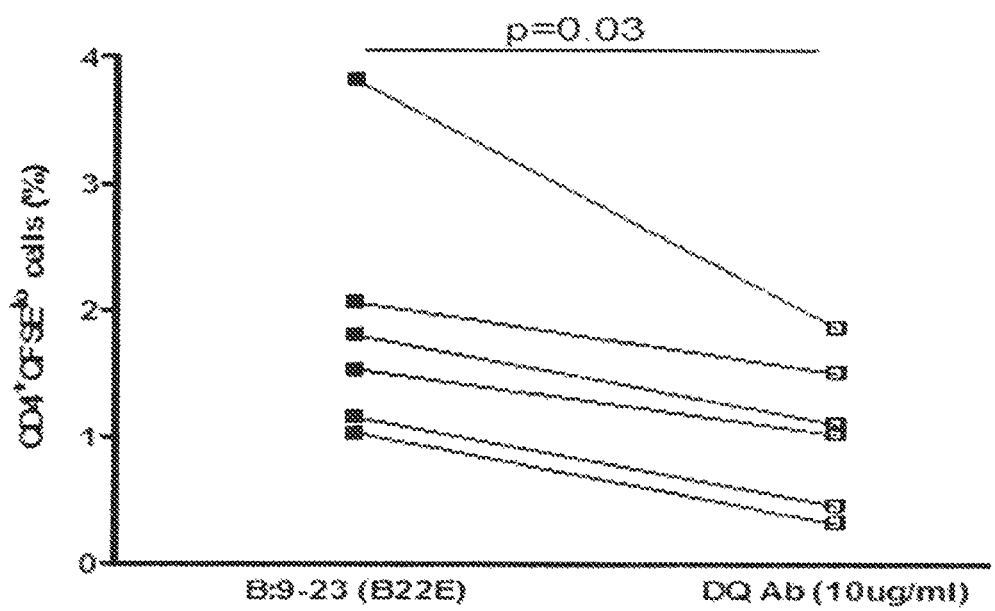

FIG. 4A shows the proliferation of unfractionated PBMCs with insulin peptides from longstanding T1D subjects with two non-β57Asp DQ alleles. Isolated and unfractionated PBMCs were labeled with CFSE, cultured without any in vitro stimulus (no cytokines, anti-CD3 or anti-CD28 antibodies) other than peptide, and analyzed by flow cytometry for CFSE dilution and cell surface markers after 7 days of culture. FIG. 4A shows representative data from two T1D subjects with CFSE proliferation assays. CD4 T cells proliferate in response to the B22E mimotope without the in vitro addition of cytokines. PBMCs labeled with CFSE (no antigen stimulus in culture) are a negative control and Pentacel (childhood vaccine containing 5 different immunogens) is a positive control. FIG. 4B shows summary data of proliferative responses comparing CFSE only (no antigen background) to the B22E mimotope, and FIG. 4C shows a proliferation of native insulin B:9-23 to the mimotope. FIG. 4D shows an inhibition curve of a DQ antibody blocking CD4 T cell proliferation from a T1D with two non-β57Asp DQ alleles (DQ8/8 homozygote). Antibody was added in culture with CFSE labeled PBMCs and B22E mimotope for the entire 7-day culture period. Percentage of inhibition was calculated from proliferation of CD4+CFSElo cells to the insulin B22E mimotope. FIG. 4E shows summative data of proliferative responses to the mimotope with and without DQ antibody.

Figure 5A:
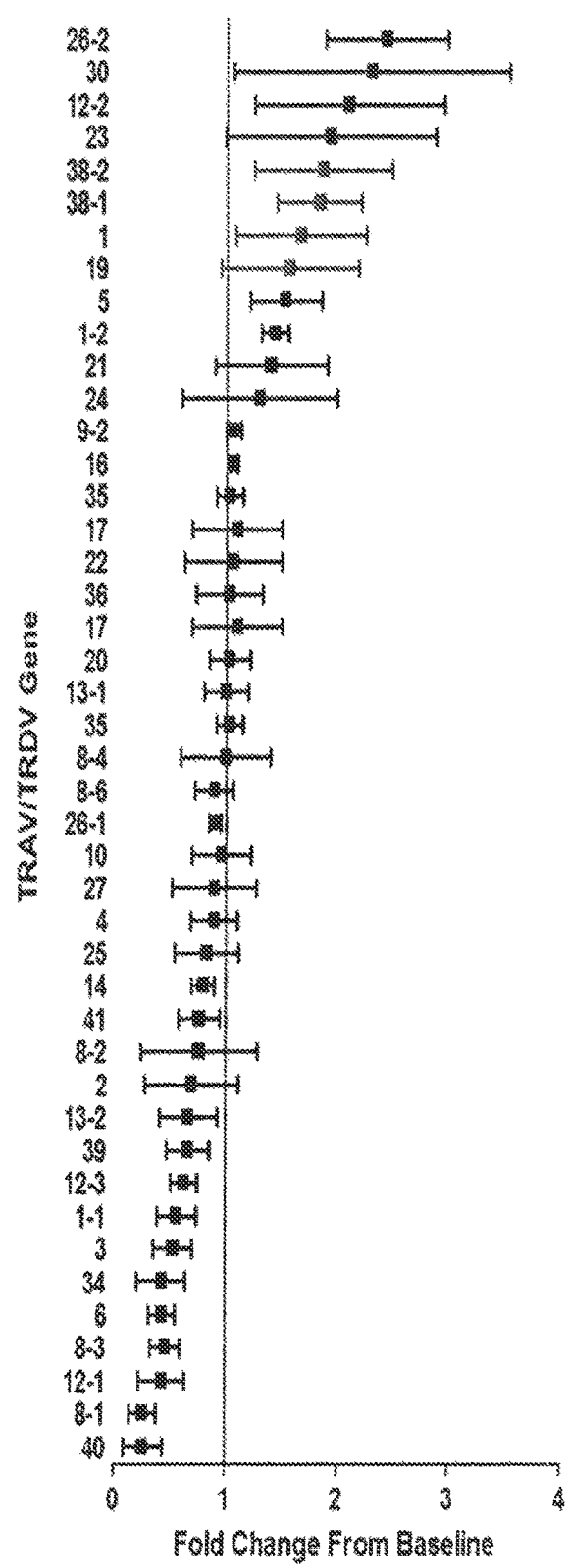

FIGS. 5A-5C show T cell receptor (TCR) V gene skewing after proliferation to the insulin B22E mimotope. FIG. 5A is summative data for Vα gene sequencing before and after stimulation from three T1D subjects all having two non-β57Asp DQ alleles. TCR alpha chain genes were sequenced to identify V gene usage (TRAV and TRDV) from CD4+ cells prior to proliferation and then on sorted CD4+CFSElo cells after proliferation to the insulin B22E mimotope. Data are depicted as the fold change (proliferated/baseline) for each V gene and show the mean+/− SEM. FIG. 5B is a phylogenetic tree of V genes based upon similarity in CDR1 and (FIG. 5C) CDR2 regions. Four predominant V genes (grey text) in the proliferated cells of all 3 patients cluster together based upon similarity in CDR1 and CDR2 sequences.

DESCRIPTION OF ILLUSTRATIVE EMBODIMENTS

The present invention is drawn to mimotopes of insulin peptides and methods of using the same to induce immunosuppression, prevent diabetes onset and monitor disease progression and treatment regimens.

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. In case of conflict, the present specification, including explanations of terms, will control. The materials, methods and examples are illustrative only and not intended to be limiting.

In order to facilitate review of the various embodiments of this disclosure, the following explanations of specific terms are provided:

Adjuvant: A substance that non-specifically enhances the immune response to an antigen. Non-limiting examples include complete Freund's adjuvant (CFA), incomplete Freund's adjuvant (IFA), aluminum salts, Amplivax (CpG oligodeoxynucleotides; Mosemann et al., *J. Immunol.* 173: 4433, 2004), and IVX-908 (ID Biomedical of Canada). Development of vaccine adjuvants for use in humans is reviewed in, for example, Singh et al. (*Nat. Biotechnol.* 17:1075-1081, 1999).

Animal: Living multi-cellular vertebrate organisms, a category that includes, for example, mammals and birds. The term mammal includes both human and non-human mammals. Similarly, the term "subject" or "patient" includes both human and veterinary subjects, for example, humans, non-human primates, dogs, cats, horses, and cows.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes.

Autoimmune Disease: A disease in which the immune system produces an immune response (for example, a B cell or a T cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces. An exemplary autoimmune diseases affecting humans includes type 1 diabetes (T1D).

Beta interferon: Any beta interferon including interferon-beta 1a and interferon-beta 1b. Interferon-beta 1a is a 166 amino acid glycoprotein with a predicted molecular weight of approximately 22,500 daltons. The interferon beta 1a known as Avonex® is produced by recombinant DNA technology utilizing mammalian cells (Chinese Hamster Ovary cells) into which the human interferon-beta gene has been introduced. The amino acid sequence of Avonex® is identical to that of natural human interferon-beta.

Cluster of differentiation factor 4 (CD 4) is a T-cell surface protein that mediates interaction with MHC class II molecules. CD4 is a 55 kDa transmembrane glycoprotein belonging to the immunoglobulin superfamily. A T-cell that expresses CD4 is a "CD4+" T-cell. Likewise, a T-cell that does not express CD4 is a "CD4−" T-cell.

Cluster of differentiation factor 25 (CD 25), the IL-2 receptor alpha chain. A T cell that expresses CD25 is a "CD25+" T cell.

Cytokine: The term "cytokine" is used as a generic name for a diverse group of soluble proteins and peptides that act as humoral regulators at nano- to picomolar concentrations and which, either under normal or pathological conditions, modulate the functional activities of individual cells and tissues. These proteins also mediate interactions between cells directly and regulate processes taking place in the extracellular environment. Many cytokines act as cellular survival factors by preventing programmed cell death. Cytokines include both naturally occurring peptides and variants that retain full or partial biological activity.

Immune response: A response of a cell of the immune system, such as a B cell, T cell, macrophage or polymorphonucleocyte, to a stimulus. An immune response can include any cell of the body involved in a host defense response for example, an epithelial cell that secretes interferon or a cytokine. An immune response includes, but is not limited to, an innate immune response or inflammation.

Immunosuppression: Nonspecific unresponsiveness of cellular and/or humoral immunity. Immunosuppression refers to the prevention or diminution of an immune response and occurs when T and/or B cells are depleted in number or suppressed in their reactivity, expansion or differentiation. Immunosuppression may arise from activation of specific or non-specific Treg cells, from cytokine signaling, in response to irradiation, or by drugs that have generalized immunosuppressive effects on T and B cells.

Immunosuppressive agent: A molecule, such as a chemical compound, small molecule, steroid, nucleic acid molecule, or other biological agent, that can decrease an immune response such as an inflammatory reaction. Immunosuppressive agents include, but are not limited to an agent of use in treating an autoimmune disorder. Specific, non-limiting examples of immunosuppressive agents are non-steroidal anti-inflammatory agents, cyclosporine A, and anti-CD4 antibodies.

Inflammation: A complex series of events, including dilatation of arterioles, capillaries and venules, with increased permeability and blood flow, exudation of fluids, including plasma proteins and leucocytic migration into the inflammatory focus.

Inflammation may be measured by many methods well known in the art, such as the number of leukocytes, the number of polymorphonuclear neutrophils (PMN), a measure of the degree of PMN activation, such as luminal enhanced-chemiluminescence, or a measure of the amount of cytokines present.

Inhibiting or Treating a Disease: Inhibiting the full development of a disease or condition, for example, in a subject who is at risk for a disease such as an autoimmune disease (e.g., T1D). "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated/purified: An "isolated" or "purified" biological component (such as a nucleic acid, peptide or protein) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell. Preferably, a preparation is purified such that the biological component represents at least 50%, such as at least 70%, at least 90%, at least 95%, or greater of the total biological component content of the preparation.

Leukocyte: Cells in the blood, also termed "white cells," that are involved in defending the body against infective organisms and foreign substances. Leukocytes are produced in the bone marrow. There are five main types of leukocytes, subdivided into two main groups: polymorphonuclear leukocytes (neutrophils, eosinophils, basophils) and mononuclear leukocytes (monocytes and lymphocytes).

Lymphocyte: Any of the mononuclear nonphagocytic leukocytes, found in the blood, lymph, and lymphoid tissues (such as the thymus), that are the body's immunologically competent cells and their precursors. Lymphocytes are divided on the basis of ontogeny and function into at least two classes, B and T lymphocytes (a.k.a., B and T cells), which are responsible for humoral and cellular immunity, respectively.

Peptide: A polymer in which the monomers are amino acid residues which are joined together through amide bonds. When the amino acids are alpha-amino acids, either the L-optical isomer or the D-optical isomer can be used. The terms "peptide" or "polypeptide" as used herein are intended to encompass any amino acid sequence and include modified sequences such as glycoproteins. The term "peptide" is specifically intended to cover naturally occurring peptides, as well as those which are recombinantly or synthetically produced. The term "residue" or "amino acid residue" includes reference to an amino acid that is incorporated into a peptide, polypeptide, or protein.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful in the methods disclosed herein are conventional. *Remington's Pharmaceutical Sciences*, by E. W. Martin, Mack Publishing Co., Easton, Pa., 15th Edition (1975), describes compositions and formulations suitable for pharmaceutical delivery of TCR peptides and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween, sodium acetate or sorbitan monolaurate.

Pulsatile Dose: A dose administered as a bolus. A pulsatile dose can be administered to a subject as a single administration, such as by direct injection or by an intravenous infusion during a specified time period. Thus, the pulsatile dose can be a "push" or rapid dose, but need not be, as it can be administered over a defined time period, such as in an infusion. Repeated pulsatile doses can be administered to a subject, such as a bolus administered repeatedly, such as about every one, two, or three months, or about every one, two, three or four weeks or about every one, two or three days in a therapeutic regimen. In this embodiment, the administered dose can be the same amount of an agent, or can be different amounts administered at several time points separated by periods wherein the agent is not administered to the subject, or wherein a decreased amount of the agent is administered to the subject.

Regulatory T Cells (Treg): CD4+CD25+ T cells that prevent the activation and/or expansion of other cell populations, for example CD4+CD25− responder T cells. Reduction or functional alteration of Treg cells leads to the spontaneous development of various organ-specific autoimmune diseases, including, for example, autoimmune thyroiditis, gastritis, and type 1 diabetes (see, for example, Sakaguchi et al., *J. Immunol.* 155:1151-64, 1995; Suri-Payer et al., *J. Immunol.* 160:1212-18, 1998; Itoh et al., *J. Immunol.* 162:5317-26, 1999). The FOXP3 transcription factor is predominantly expressed by the Treg cell lineage (Fontenot et al., *Nature Immunol* 4:330-36, 2003; Hon et al., *Science* 299:1057-61, 2003).

Responder T Cells: A subpopulation of mature T cells that facilitate an immune response through cell activation and/or the secretion of cytokines. In one embodiment, the responder T cells are CD4+CD25− T cells. In another embodiment, the responder T cells are CD8+CD25− T cells. One specific, non-limiting example of a responder T cell is a T lymphocyte that proliferates upon stimulation by antigen or a stimulator cell, such as an allogenic stimulator cell. Another specific, non-limiting example of a responder T cell is a T lymphocyte whose responsiveness to stimulation can be suppressed by Treg cells.

Sample: A portion, piece, or segment that is representative of a whole. This term encompasses any material, including for instance samples obtained from a subject. A "biological sample" is a sample obtained from a subject. As used herein, biological samples include all clinical samples useful for detection of cytokine or Foxp3+ regulatory T cells in subjects, including, but not limited to, cells; tissues; bodily fluids, such as blood, derivatives and fractions of blood, such as serum; and biopsied or surgically removed tissue, including tissues that are, for example, unfixed, frozen, fixed in formalin and/or embedded in paraffin. In particular embodiments, the biological sample is obtained from a subject, such as blood or serum.

Subject: A human or non-human animal. In one embodiment, the subject has an autoimmune disease, such as type 1 diabetes (T1D).

Symptom and sign: Any subjective evidence of disease or of a subject's condition, that is, such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for immunological status or the presence of lesions in a subject with an autoimmune disease (e.g., T1D).

T Cell: A lymphoid cell that mediates cell-mediated immune responses in the adaptive immune system. Adaptive cell-mediated immunity is immunity that confers resistance to pathogenic conditions (including, for example, neoplasia or infection by microbes, viruses, or bacteria) that are not susceptible to the innate immune response (for example, not susceptible to the antibody-making cells of the immune system). T cells mature in the thymus, circulate between blood and lymph, populate secondary lymphoid tissues, and are recruited to peripheral sites of antigen exposure. T cells generally cannot recognize foreign antigens without the help of antigen presenting cells (APC), such as macrophages, dendritic cells or B-cells that present antigen in conjunction with major histocompatibility complex.

T Cell Receptor (TCR) and TCR Receptor Peptides: Membrane-bound proteins composed of two transmembrane chains that are found on T cells. The T cell receptor recognizes antigen peptides presented in the context of the Major Histocompatibility Complex (MHC) proteins. In the case of CD4+ T cells, the antigen peptides must be presented on Class II MHC, and in the case of CD8+ T cells, the antigen peptides must be presented on Class I MHC. The T cell antigen receptor consists of either an alpha/beta chain or a gamma/delta chain associated with the CD3 molecular complex. The two transmembrane chains consist of two domains, called a "variable" and a "constant" domain, and a short hinge that connects the two domains. The V domains include V-, D-, and J-immunoglobulin like elements in the β chain and V- and J-like elements in the α chain.

Therapeutically effective amount: A quantity of a specified agent sufficient to achieve a desired effect in a subject being treated with that agent. For example, this can be the amount of one or more TCR peptides useful in preventing, ameliorating, and/or treating an autoimmune disorder (e.g., MS) in a subject. Ideally, a therapeutically effective amount of an agent is an amount sufficient to prevent, ameliorate, and/or treat an autoimmune disorder (e.g., MS) in a subject without causing a substantial cytotoxic effect in the subject. The effective amount of an agent useful for preventing, ameliorating, and/or treating an autoimmune disorder (e.g., MS) in a subject will be dependent on the subject being treated, the severity of the disorder, and the manner of administration of the therapeutic composition.

II. Overview of Aspects of the Invention

An aspect of the invention is a method for detecting in a subject a predisposition to an autoimmune disease. In one embodiment, this method includes detecting, in response to a peptide of Table 1, an inflammatory response, with IFN-γ production, in a biological sample from the subject that differs from a reference level of IFN-γ production in a biological sample from a subject with no predisposition to an autoimmune disease. In another embodiment, this method includes detecting, in response to a peptide of Table 1, a dominant IL10 regulatory response in a biological sample from the subject that differs from a reference level of IL10 production in a biological sample from a subject with no predisposition to an autoimmune disease. In another embodiment, this method includes detecting, in response to a peptide of Table 1, the ratio of IFN-γ to IL10 in a biologic sample from the subject that differs from a reference level of IFN-γ/IL10 in a biological sample from a subject with no predisposition to an autoimmune disease. The HLA-DQ genotype of the subject may be determined in conjunction with detecting the response to a peptide of Table 1. In these embodiments, the HLA-DQ genotyping may be conducted prior to, after, or simultaneous with the detection of the subject's response to a peptide of Table 1. In specific embodiments, the autoimmune disease is type 1 diabetes (T1D).

TABLE 1

Human Insulin β-chain Mimotopes

| SEQ ID NO | Peptide Sequence | Description |
|---|---|---|
| 1 | SHLVEALYLVCGERG | B:9-23 wild type human |
| 2 | SHLVEALYLVCGEEG | B:9-23 mimotope; B22 arginine to glutamic acid |
| 3 | SHLVEALYLVCGGEG | B:9-23 mimotope; B21-22 glutamic acid-arginine to glycine-glutamic acid |
| 4 | SHLVEELYLVCGEEG | B:9-23 mimotope; B14;22 alanine to glutamic acid and arginine to glutamic acid |
| 5 | SHLVEELYLVCGERG | B:9-23 mimotope; B14 alanine to glutamic acid |
| 6 | SHLVGELYLVCGERG | B:9-23 mimotope; B13-14 glutamic acid-alanine to glycine-glutamic acid |
| 7 | SHLVGELYLVCGGEG | B:9-23 mimotope; B13-14;21-22 glutamic acid-alanine to glycine-glutamic acid and glutamic acid-arginine to glycine-glutamic acid |
| 8 | SHLVGALYLVCGGEG | B:9-23 mimotope; B13;21-22 glutamic acid to glycine and glutamic acid-arginine to glycine-glutamic acid |
| 9 | SHLVGELYLVCGGRG | B:9-23 mimotope; B13-14;21 glutamic acid-alanine to glycine-glutamic acid and glutamic acid to glycine |
| 10 | SHLVEALYLVAGEEG | B:9-23 mimotope; B19 cysteine to alanine to prevent peptide dimerization; B22 arginine to glutamic acid |
| 11 | SHLVEALYLVAGGEG | B:9-23 mimotope; B19 cysteine to alanine to prevent peptide dimerization; B21-22 glutamic acid-arginine to glycine-glutamic acid |
| 12 | SHLVEALYLVAGAEG | B:9-23 mimotope; B19 cysteine to alanine to prevent peptide dimerization; B21-22 glutamic acid-arginine to alanine-glutamic acid |
| 13 | SHLVEALYLVAGVEG | B:9-23 mimotope; B19 cysteine to alanine to prevent peptide dimerization; B21-22 glutamic acid-arginine to valine-glutamic acid |
| 14 | SHLVEALYLVAGLEG | B:9-23 mimotope; B19 cysteine to alanine to prevent peptide dimerization; B21-22 glutamic acid-arginine to leucine-glutamic acid |
| 15 | SHLVEALYLVAEAEG | B:9-23 mimotope; B19-22 cysteine-glycine-glutamic acid-arginine to alanine-glutamic acid-alanine-glutamic acid |

TABLE 1-continued

Human Insulin β-chain Mimotopes

| SEQ ID NO | Peptide Sequence | Description |
|---|---|---|
| 16 | SHLVEALYLV<u>AAED</u>G | B:9-23 mimotope; B19-22 cysteine-glycine-glutamic acid-arginine to alanine-alanine-glutamic acid-aspartic acid |
| 17 | SHLVEALYLV<u>AQVE</u>G | B:9-23 mimotope; B19-22 cysteine-glycine-glutamic acid-arginine to alanine-glutamine-valine-glutamic acid |
| 18 | SHLVEALYLV<u>AALE</u>G | B:9-23 mimotope; B19-22 cysteine-glycine-glutamic acid-arginine to alanine-alanine-leucine-glutamic acid |
| 19 | SHLVEALYLV<u>EAED</u>G | B:9-23 mimotope; B19-22 cysteine-glycine-glutamic acid-arginine to glutamic acid-alanine-glutamic acid-aspartic acid |
| 20 | SHLVEALYLV<u>GQVE</u>G | B:9-23 mimotope; B19-22 cysteine-glycine-glutamic acid-arginine to glycine-glutamine-valine-glutamic acid |
| 21 | SHLVEALYLV<u>LALE</u>G | B:9-23 mimotope; B19-22 cysteine-glycine-glutamic acid-arginine to leucine-alanine-leucine-glutamic acid |

Another aspect of the invention is a method for diagnosing T1D in a subject. This method includes detecting, in response to a peptide of Table 1, an inflammatory response, with IFN-γ production, in a biological sample from the subject that differs from a reference level of IFN-γ production in a biological sample from a control subject (i.e., a subject known not to have T1D). In these embodiments, the detection of IFN-γ production in response to the peptide of Table 1 is indicative of T1D in the subject (i.e., the subject is diagnosed with T1D). In another embodiment, this method includes detecting, in response to a peptide of Table 1, a dominant IL10 regulatory response in a biological sample from the subject that differs from a reference level of IL10 production in a biological sample from a control subject (i.e., a subject known not to have T1D). In another embodiment, the method includes detecting, in response to a peptide of Table 1, an IFN-γ/IL10 ratio in a biological sample from the subject that differs from a reference level of IFN-γ/IL10 in a biological sample from a control subject (i.e., a subject known not to have T1D). In these embodiments, the detection of IFN-γ production or a ratio of IFN-γ/IL10 in response to the peptide of Table 1 is indicative of no T1D in the subject (i.e., the subject is not diagnosed with T1D, the subject is identified as non-diabetic). The HLA-DQ genotype of the subject may be determined in conjunction with detecting the response to a peptide of Table 1. In these embodiments, the HLA-DQ genotyping may be conducted prior to, after or simultaneous with the detection of the subject's response to a peptide of Table 1.

Another aspect of the invention is a method for assessing the efficacy of a therapy for an autoimmune disease. This method includes determining that an inflammatory response, with IFN-γ production or IFN-γ/IL10 ratio, in response to a peptide of Table 1, in a first biological sample taken from a subject differs from the inflammatory response, with IFN-γ production, in response to a peptide of Table 1, in a second biological sample taken from the subject after a period of treatment with the therapy for the autoimmune disease, wherein a difference in the inflammatory response, with IFN-γ production or IFN-γ/IL10 in the first biological sample as compared to the second biological sample assesses the efficacy of the therapy for the autoimmune disease. In a specific example, the therapy comprises administration of a therapeutically effective amount of a peptide of Table 1, including administration of insulin to the subject.

Another aspect of the invention is a method for inhibiting or treating T1D. In one embodiment, the method includes administering to a subject diagnosed with or suspected of having or developing T1D, a therapeutically effective amount of a composition comprising a peptide of Table 1, thereby inhibiting T1D in the subject. In a specific embodiment, the composition includes a therapeutically effective amount of a peptide of SEQ ID NO:2. In related embodiments, the subject is first identified as having T1D by methods that include detecting, in response to a peptide of Table 1, an inflammatory response, with IFN-γ production or an IFN-γ/IL10 ratio, in a biological sample from the subject.

Another aspect of the invention is a method for inducing immunosuppression in a subject having or suspected of having an autoimmune disease. This method includes administering to a subject a therapeutically effective amount of a composition comprising a peptide of Table 1, thereby inducing immunosuppression in the subject. In specific embodiments, the subject has, or is suspected of developing, T1D. In specific embodiments, the autoimmune disease is T1D. In related embodiments, the subject is first identified as having T1D by methods that include detecting, in response to a peptide of Table 1, an inflammatory response, with IFN-γ production or IFN-γ/IL10 ratio, in a biological sample from the subject.

Diagnostic Methods and Method for Monitoring Treatment

It is disclosed herein that T cell responses to contact with a peptide of Table 1 differ between subjects with type 1 diabetes (T1D) and healthy controls (i.e., non-diabetic subjects). Accordingly, it is now possible to use these T cell responses to detect T1D, or a predilection to T1D in a subject, and/or to monitor the efficacy of T1D therapies. These methods can include determining whether the T cell responses in one or more biological samples taken from a subject differ from each other or from another reference point. The reference point can be a standard value, or a control with a known T cell response (i.e., a T cell response from a subject confirmed type diabetic or non-diabetic). However, the reference point can also be another sample from the same subject. For example, prior to the onset of a T1D therapy, a first sample is taken from the subject. Following onset of therapy, a second sample is taken from the subject. The T cell responses are evaluated in the first sample and in the second sample. If the T cell responses are indicative of an inflammatory response (e.g., with IFN-$\gamma$ production or increased IFN-$\gamma$/IL10 ratio) in the second sample as compared to the first sample, the therapy is not having the desired effect (and thus could be discontinued). However, if the T cell responses are indicative of a reduction in inflammatory response (e.g., with reduced IFN-$\gamma$ production or IFN-$\gamma$/IL10) or an IL10 regulatory T cell response in the first sample as compared to the second sample, then the therapy is having the desired effect (and thus may be continued).

A biological sample that is useful in these methods includes any part of the subject's body that can be obtained and reduced to a form that can be analyzed for the T cell response. Typically, a biological sample will contain T cells in amounts sufficient to conduct the desired analysis. The T cells of use in these methods can be derived from any convenient T cell source in the subject, such as lymphatic tissue, spleen cells, blood, or pancreas. The T cells can be enriched, if desired, by standard positive and negative selection methods. If enriched, the T cell population should retain a sufficient number of antigen-presenting cells to present the TCR peptide to the regulatory T cells. A convenient source of T cells to use in these methods are peripheral blood mononuclear cells (PBMC), which can be readily prepared from blood by density gradient separation, by leukapheresis or by other standard procedures known in the art. Thus, suitable biological samples include, for example, blood, or the components of blood, such as serum or isolated white blood cells. The biological sample may contain T cells in the peripheral blood. In specific embodiments, the biological sample is unfractionated peripheral blood mononuclear cells (PBMCs). Biological samples can be obtained from normal, healthy subjects or from subjects who are predisposed to or who are suffering from T1D. The disclosed methods contemplate as a subject any living organism capable of experiencing an autoimmune disease, including veterinary subjects (such as, felines, canines, rodents (e.g., mice and rats), equines, bovines, ovines, and the like) and human subjects (including, adults, adolescents, and children).

In one embodiment, at least two biological samples are obtained from a single subject over time, such as during a therapeutic regimen. In one non-limiting example, the samples are obtained from the same subject during the administration of a pulsatile doses of any therapeutic agent. The T cell response to a peptide of Table 1 is assessed in the first sample and the second sample. An absent or reduced T cell response indicative of inflammation in the second sample as compared to the first sample indicates that the therapy is effective. An increased or substantially similar T cell response indicative of inflammation in the second sample indicates that the therapy is ineffective.

A variety of T1D therapies that are administered over a specified time period can be evaluated using the methods disclosed herein. In some embodiments, at least two biological samples are obtained from a single subject over time, such as during a therapeutic regimen. In one embodiment, the samples are obtained from the same subject during the administration of a maintenance therapy. A reduction in the inflammatory T cell response to contact with a peptide of Table 1 in the second sample as compared to the first sample indicates that the therapy is effective, and maintains desired clinical effect. A substantial decrease or elimination of the T cell response indicates that the therapeutic agent is effective and suggests that the dose of the therapeutic agent could be lowered to possibly achieve the desired therapeutic effect. An increase in the inflammatory T cell response to contact with a peptide of Table 1 in the second sample as compared to the first sample indicates that the therapy is not effective, and indicates that the dose of the agent is insufficient or that a different therapeutic agent should be utilized in the subject.

The T cell response to contact with a peptide of Table 1 can be detected in a variety of methods known to those of skill in the art for the detection of T cell responses indicative of inflammation, including the expression of specific cytokines.

In particular examples, the level, ratio, or activity of IFN-$\gamma$ and/or IL10 production is detected in response to contact with the native insulin B:9-23 peptide and one or more insulin mimotopes set forth in Table 1. IFN-$\gamma$ and/or IL10 protein(s) may be evaluated by standard methods (for example, using an antibody array, immunofluorescence, Western blot, radioimmunoassay, sandwich immunoassays (including ELISA), Western blot, affinity chromatography (affinity ligand bound to a solid phase), in situ detection with labeled antibodies, or any of a number of functional assays described herein).

An inflammatory T cell response (measured by evaluation of a nucleic acid transcript or protein level) and/or activity (protein) may be different with respect to a reference level of expression and/or activity of a specific cytokine. A variety of reference points can be used. In some instances, a reference point is the expression and/or activity of the cytokine in a biological sample collected from a subject not suffering from an autoimmune disease (such as a control subject). In other examples, a reference point is an average (or "normal-range") value for the expression and/or activity of the cytokine in subjects not suffering from an autoimmune disease, which normal-range value has been determined from population studies. The control may be a standard value, such as a sample with a known amount of mRNA or protein. In particular applications, such as some methods for determining the efficacy of an autoimmune disease therapy, a reference also can be, for example, the expression and/or activity of a cytokine in a biological sample from the subject prior to onset of the therapy, and/or after some period of time following (or during) the therapy. Alternatively, the efficacy of an autoimmune disease therapy can be determined by comparing the expression and/or activity of the cytokine in a test subject, who is receiving therapy, as compared to a second subject suffering from an autoimmune disease, who is receiving a placebo rather than therapy. In this latter situation, it is expected that the expression levels and/or activities of the cytokine in the treated subject would diverge from those of a placebo-treated subject, with such expression levels and/or activities in an effectively treated subject approaching corresponding values observed in a healthy control subject. The autoimmune disease may be T1D. The cytokine may be at least one of IFN-$\gamma$ and/or IL10.

The expression level and/or activity of the cytokine (e.g., gene, transcript or protein) may differ from a reference expression level and/or activity by at least ±10%; for example, by at least about ±15%, at least about 25%, at least about 40%, at least about ±50%, at least about ±60%, at least about ±75%, or at least about ±90%.

In methods of this disclosure, IFN-γ levels are measured. A variety of methods can be used to detect and quantify IFN-γ expression by T cells. In some embodiments, IFN-γ mRNA is measured. IFN-γ mRNA can be measured by any method known to one of skill in the art. For example, polymerase chain reaction (PCR) can be used. Briefly, total RNA is extracted from T cells by any one of a variety of methods well known to those of ordinary skill in the art. Sambrook et al. (*In Molecular Cloning: A Laboratory Manual*, CSHL, New York, 1989) and Ausubel et al. (In *Current Protocols in Molecular Biology*, Greene Publ. Assoc. and Wiley-Intersciences, 1992) provide descriptions of methods for RNA isolation. The extracted RNA is then used as a template for performing reverse RT-PCR amplification of IFN-γ cDNA. IFN-γ-specific primers for the PCR reaction can be obtained, for example, from Applied Biosystems (Foster City, Calif.). Methods and conditions for PCR are described in Kawasaki et al., (In *PCR Protocols, A Guide to Methods and Applications*, Innis et al. (eds.), 21-27, Academic Press, Inc., San Diego, Calif., 1990). In other examples, Northern blotting or RNA dot blots can also be used to detect IFN-γ mRNA.

Additional methods for measuring IFN-γ expression levels utilizes measurements of IFN-γ protein. Antibodies to IFN-γ can be used in methods such as immunoassays (for example RIAs and ELISAs), immunohistochemistry, and Western blotting to assess the expression of IFN-γ.

For Western blotting, total cellular protein is extracted from T cells and electrophoresed on a sodium dodecyl sulfate-polyacrylamide gel. The proteins are then transferred to a membrane (for example, nitrocellulose or PVDF) by Western blotting, and an anti-IFN-γ antibody (e.g., a rabbit anti-human IFN-γ antibody) preparation is incubated with the membrane. After washing the membrane to remove non-specifically bound antibodies, the presence of specifically bound antibodies is detected by the use of (by way of example) an anti-rabbit antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase.

One method embodiment for detecting or diagnosing in a subject an autoimmune disease, or a predisposition to an autoimmune disease, involves (a) determining the expression and/or activity of IFN-γ (e.g., gene, transcript and/or protein) in a biological sample from a subject; and (b) comparing the expression and/or activity of the IFN-γ in the biological sample to the expression and/or activity of the IFN-γ in a reference sample, wherein a difference in the expression and/or activity of the IFN-γ in the biological sample and the reference sample detects or diagnoses an autoimmune disease or a predisposition to an autoimmune disease in the subject.

In another method embodiment, the efficacy of an autoimmune disease therapy can be determined by (a) obtaining a first biological sample from a first subject suffering from an autoimmune disease; (b) treating the first subject with a candidate therapy; (c) obtaining a second biological sample from at least one of the following: (i) the first subject following treatment; (ii) an individual not suffering from an autoimmune disease; or (iii) a second subject suffering from an autoimmune disease receiving a placebo rather than therapy; and (d) comparing the expression and/or activity of IFN-γ in the first and second biological samples after contact with a peptide of Table 1, wherein a change in the expression and/or activity of IFN-γ indicates that the candidate therapy is effective at treating the autoimmune disease in the first subject. In other methods, steps (a)-(d) can be repeated on the first subject after altering the dose or dosing regimen of the candidate therapy.

In more specific embodiments, a method for monitoring an outcome of an autoimmune disease therapy in a subject, involves (a) obtaining a first biological sample from a subject suffering from T1D; (b) treating the subject with a T1D therapy; (c) obtaining a second biological sample from the subject following a period of treatment with the T1D therapy; and (d) comparing the expression and/or activity of IFN-γ in response to contact with a peptide of Table 1, in the first and second biological samples, wherein a relative change in the expression and/or activity of IFN-γ in the first and second biological sample monitors an outcome of the candidate therapy.

In some embodiments, T cells are isolated from the sample prior to performing the assay for T cell response to contact with a peptide of Table 1. The T cells can be any T cells of interest, such as, but not limited to, CD3+, CD4+, and/or CD25+ T cells. In one specific non-limiting example, CD4+CD25+ T cells can be isolated, and the expression of IFN-γ can be assessed in the CD4+CD25+ T cells.

Methods for the isolation and quantitation of T cells, are well known in the art. Typically, labeled antibodies specifically directed to one or more cell surface markers are used to identify and quantify the T cell population. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate (FITC), tetramethylrhodamine isothiocyanate, phycoerythrin (PE), allophycocyanins and Texas Red. For additional fluorochromes that can be conjugated to antibodies see Haugland, R. P., *Handbook of Fluorescent Probes and Research Products*, published by Molecular Probes, 9$^{th}$ Edition (2002). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include, but are not limited to, technetium 99 ($^{99}$Tc), $^{125}$I, and amino acids comprising any radionuclides, including, but not limited to, $^{14}$C, $^{3}$H and $^{35}$S.

Fluorescence activated cell sorting (FACS) can be used to sort cells that are CD4+, CD25+, or both CD4+ and CD25+, by contacting the cells with an appropriately labeled antibody. However, other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Additional separation procedures may include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic Petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well known in the art.

Unbound cells then can be eluted or washed away with physiologic buffer after sufficient time has been allowed for the cells expressing a marker of interest (e.g., CD4 and/or CD25) to bind to the solid-phase linked antibodies. The bound cells are then separated from the solid phase by any appropriate method, depending mainly upon the nature of the solid phase and the antibody employed, and quantified using methods well known in the art. In one specific, non-limiting example, bound cells separated from the solid phase are quantified by FACS.

Antibodies may be conjugated to biotin, which then can be removed with avidin or streptavidin bound to a support, or fluorochromes, which can be used with FACS to enable cell separation and quantitation, as known in the art.

In additional embodiments, cytokine expression levels in the biological sample of interest are measured using any one of a variety of standard methods used to detect and quantify cytokine expression by T-cells. For example, an immunospot assay, such as the enzyme-linked immunospot or "ELISPOT" assay, can be used. The immunospot assay is a highly sensitive and quantitative assay for detecting cytokine secretion at the single cell level. Immunospot methods and applications are well known in the art and are described, for example, in Czerkinsky et al., *J. Immunol. Methods* 110:29-36, 1988; Olsson et al. *J. Clin. Invest.* 86:981-985, 1990; and EP 957359.

The immunospot assay uses microtiter plates containing membranes that are precoated with a capture agent, such as an anti-cytokine antibody, specific for the cytokine to be detected. T cells of interest are plated together with a composition (e.g., an effective amount of a peptide of Table 1). The T cells that respond to the composition secrete various cytokines. As a cytokine to be quantified is locally released by the T cells, it is captured by the membrane-bound antibody. After a suitable period of time the cell culture is terminated, the T cells are removed and the plate-bound cytokine is visualized by an appropriate detection system. Each cytokine-secreting T cell will ideally be represented as a detectable spot. The number of spots, and thus the number of T cells secreting the particular cytokine of interest, can be counted manually (for example, by visualization via light microscopy) or by using an automated scanning system (for example, an Immunospot Reader).

Variations of the standard immunospot assay are well known in the art and can be used to detect alterations in cytokine production in the methods of the disclosure. For example, U.S. Pat. No. 5,939,281 (which is incorporated herein by reference) describes an improved immunospot assay that uses a hydrophobic membrane instead of the conventional nitrocellulose membrane, to bind the cytokine capture reagent. This variation can be used to reduce the non-specific background and increase the sensitivity of the assay. Other modifications to the standard immunospot assay that increase the speed of processing multiple samples, decrease the amount of reagents and T cells needed in the assay, or increase the sensitivity or reliability of the assay, are contemplated herein and can be determined by those skilled in the art.

U.S. Pat. No. 6,218,132 (which is incorporated herein by reference) describes a modified immunospot assay in which T cells are allowed to proliferate in response to stimulation before detection of the cytokine of interest. This method, although more time-consuming, can be used to increase the sensitivity of the assay for detecting T cells present at a low frequency in the starting population.

Antibodies suitable for use in immunospot assays, which are specific for secreted cytokines (such as IFN-γ and/or IL10), as well as detection reagents and automated detection systems, are well known in the art and generally are commercially available. Appropriate detection reagents are also well known in the art and commercially available, and include, for example, secondary antibodies conjugated to fluorochromes, colored beads, and enzymes whose substrates can be converted to colored products (for example, horseradish peroxidase and alkaline phosphatase). Other suitable detection reagents include secondary agents conjugated to ligands (for example, biotin) that can be detected with a tertiary reagent (for example, streptavidin) that is detectably labeled as above.

Other methods for detecting and quantifying cytokine expression are well known in the art, and can be used as an alternative to immunospot assays. Such methods include the enzyme-linked immunoabsorbent assay (ELISA), which can be used to measure the amount of cytokine secreted by T cells into a supernatant (see, e.g., Vandenbark et al., *Nature Med.* 2:1109-1115, 1996). Alternatively, the expression of cytokine mRNA can be determined by standard immunological methods, which include reverse transcriptase polymerase chain reaction (RT-PCR) and in-situ hybridization (as described above).

In the methods disclosed herein, suppression of cell proliferation by T cells from the sample of interest can also be measured. Suppression of proliferation can be evaluated using many methods well known in the art. In one embodiment, T cell proliferation is quantified by measuring [$^3$H]-thymidine incorporation. Proliferating cells incorporate the labeled DNA precursor into newly synthesized DNA, such that the amount of incorporation, measured by liquid scintillation counting, is a relative measure of cellular proliferation. In another embodiment, cell proliferation is quantified using the thymidine analogue 5-bromo-2'-deoxyuridine (BrdU) in a proliferation assay. BrdU is incorporated into cellular DNA in a manner similar to thymidine, and is quantified using anti-BrdU mAbs in an ELISA.

Method for Inhibiting an Autoimmune Disease

Another aspect of the invention provides methods for inhibiting an autoimmune disease. These methods include administering to a subject in need thereof a therapeutically effective amount of a composition that decreases T-cell inflammatory response to contact with a peptide of Table 1, thereby inhibiting the autoimmune disease. The autoimmune disease may be T1D.

The composition can include a single peptide of Table 1, or multiple peptides of Table 1. The peptides may include peptides having at least 90% homology to a peptide sequence of those peptides set forth in Table 1, and which stimulate T cells that are reactive against insulin, to convert naive T cells into Foxp3+ regulatory T cells and prevent diabetes onset. The peptides may include fragments of the peptides of Table 1 that retain the ability to stimulate T cells that are reactive against insulin, to convert naive T cells into Foxp3+ regulatory T cells and prevent diabetes onset. The peptides may include insulin peptides, including insulin, proinsulin, and/or the insulin β chain, having at least one amino acid substitution of SEQ ID NOs: 2-9, and which stimulate T cells that are reactive against insulin, to convert naive T cells into Foxp3+ regulatory T cells and prevent diabetes onset. An exemplary peptide includes the amino acid sequence set forth in SEQ ID NO:2. Appropriate peptides to use in the methods disclosed herein can be determined by those skilled in the art. The immunogenicity of a given peptide can be predicted using well-known algorithms that predict T cell epitopes (see, e.g., Savoie et al., *Pac. Symp. Biocomput.* 1999:182-89, 1999; Cochlovius et al., *J. Immunol.* 165:4731-41, 2000). Both the immunogenicity and the specificity of a given peptide can be confirmed by standard immunological assays that measure in vivo or in vitro T cell responses (e.g., T cell proliferation assays, delayed type hypersensitivity assays, ELISA assays, ELISPOT assays and the like).

The composition(s) containing the peptide(s) can be formulated as a vaccine. In these embodiments, the formulation may also include a therapeutically effective amount of an adjuvant, such as, but not limited to, complete Freund's adjuvant (CFA), incomplete Freund's adjuvant (IFA), immunomodulatory oligonucleotides including Immunomers (Wang et al., Int J Oncol 2004, 24: 901-08.) and CpG oligodeoxynucleotides (Mosemann et al., J. Immunol. 173: 4433, 2004), or IVX-908 (ID Biomedical of Canada). Further additional agents that can be administered to the subject include, for example, a therapeutically effective amount of: an interferon (such as IFN β1a or IFN β1b), an interleukin (such as IL-4), an antibody to an interleukin (such as anti-IL-12 or anti-IL-23), Glatiramer acetate (also known as Copolymer 1), Natalizumab, and/or Mitoxantrone.

In one embodiment, an additional therapeutic agent is administered to the subject with an autoimmune disorder. These therapeutic agents can be administered at the same time, or at a different time (sequentially) as the peptide of Table 1 that increases the production of Foxp3+ regulatory T cells. These agents may include, but are not limited to, interferon-beta. These agents can be included in the same composition as the peptide of Table 1 that increases the production of Foxp3+ regulatory T cells, or can be administered in separate compositions.

Administration of a therapeutically effective amount of the peptide of Table 1 that increases the production of Foxp3+ regulatory T cells can be utilized whenever desired, for example, at the first sign of symptoms of an autoimmune disease, such as T1D, or at the first sign of symptoms of inflammation or insulin-specific antibodies, or T cell mediated destruction of insulin producing beta cells within pancreatic islets, or the detection of CD4 T cells targeting pancreatic beta cells, or the presence of CD4 T cells in the pancreas and/or pancreatic lymph nodes of a subject.

Alternatively, administration of a therapeutically effective amount of the peptide of Table 1 that increases the production of Foxp3+ can be done prophylactically (i.e., before any overt systems of autoimmune disease onset).

Therapeutically effective amounts of the peptide of Table 1 that increases the production of Foxp3+ can be administered by a number of routes, including parenteral administration, for example, intravenous, intraperitoneal, intramuscular, intradermal, intrasternal, or intraarticular injection, or infusion. One of skill in the art can readily determine the appropriate route of administration.

The therapeutically effective amount of the peptide of Table 1 that increases the production of Foxp3+ will be dependent upon the subject being treated, the severity and type of the affliction, and the manner of administration. For example, a therapeutically effective amount of a peptide of Table 1 can vary from about 1-500 µg/injection. The exact amount of the peptide is readily determined by one of skill in the art based on the age, weight, sex, and physiological condition of the subject. Effective doses can be extrapolated from dose-response curves derived from in vitro or animal model test systems.

Generally, a therapeutically effective amount of the peptide of Table 1 that increases the production of Foxp3+, is that amount of the peptide that inhibits the advancement, or causes regression of T1D, or which is capable of relieving symptoms caused by an autoimmune disease. For example, a therapeutically effective amount of the peptide of Table 1 that increases the production of Foxp3+, is that amount of the peptide that is capable of inducing tolerance in a diabetic or pre-diabetic subject.

The peptide of Table 1 that increases the production of Foxp3+ can be administered in a pharmaceutically acceptable carrier, such as buffered saline or another medium suitable for administration to a subject. For example, one or more peptides of Table 1 can be administered in a pharmaceutically acceptable carrier, such as a carrier formulated for injection. It should be noted that a single peptide of Table 1 that increases the production of Foxp3+ can be administered, or multiple peptides can be administered to a subject of interest (such as a subject with or suspected of having T1D).

In one embodiment, the peptide of Table 1 that increases the production of Foxp3+ can be administered in conjunction with one or more additional pharmaceutical agents. The additional pharmaceutical agents can be administered at the same time as, or sequentially with, the peptide of Table 1. In one embodiment, the additional pharmaceutical agent is an additional immunosuppressive agent. When administered at the same time, the additional pharmaceutical agent(s) can be formulated in the same composition that includes the peptide of Table 1. For, example, additional pharmaceutical agents may include immunosuppressive agents (for example, azathioprine or glucocorticoids, such as dexamethasone or prednisone), anti-inflammatory agents (for example, glucocorticoids such as hydrocortisone, dexamethasone or prednisone, or non-steroidal anti-inflammatory agents such as acetylsalicylic acid, ibuprofen or naproxen sodium), cytokines (for example, interleukin-10 and transforming growth factor-β), or a vaccine.

Those skilled in the art can determine an appropriate time and duration of therapy that includes the administration of a peptide of Table 1 to achieve the desired preventative or ameliorative effects on the immune pathology.

In a specific embodiment, the method includes administering to a subject a therapeutically effective amount of a peptide comprising SEQ ID NO:2 to induce immunosuppression in a subject. An adjuvant can optionally be included with the peptide comprising SEQ ID NO:2.

Immunosuppression in the subject can be evaluated using methods well known in the art. In one embodiment, a white blood cell count (WBC) is used to determine the responsiveness of the subject's immune system. A WBC measures the number of white blood cells in a subject. Using methods well known in the art, the white blood cells in a subject's blood sample are separated from other blood cells and counted. Normal values of white blood cells are about 4,500 to about 10,000 white blood cells/µl. Lower numbers of white blood cells can be indicative of a state of immunosuppression in the subject.

In another embodiment, immunosuppression in a subject may be determined using a T lymphocyte count. Using methods known in the art, the white blood cells in a subject's blood sample are separated from other blood cells. T lymphocytes are differentiated from other white blood cells using standard methods in the art, such as, for example, immunofluorescence or FACS. Reduced numbers of T cells, or a specific population of T cells can be used as a measurement of immunosuppression. In one embodiment the population of T cells monitored or suppressed are those T cells that recognize and destroy insulin producing beta cells in pancreatic islets. A reduction in the number of such T-cells, or in the general population of T cells, compared to the number of T cells (or the number of cells in the specific population) prior to treatment can be used to indicate that immunosuppression has been induced.

In another embodiment, effective treatment or inhibition of inflammation or immunosuppression in the subject can be assayed by measuring cytokine levels in the subject. Cytokine levels in body fluids or cell samples are determined by conventional methods. For example, an immunospot assay, such as the enzyme-linked immunospot or "ELISPOT" assay, as described herein, can be used. The cytokine(s) measured may include at least one of IFN-γ and IL10.

The invention now being generally described will be more readily understood by reference to the following examples, which are included merely for the purposes of illustration of aspects of the embodiments of the present invention. The examples are not intended to limit the invention, as one of skill in the art would recognize from the above teachings and the following examples that other techniques and methods can satisfy the claims and can be employed without departing from the scope of the claimed invention.

EXAMPLES

Example 1: Detection of Robust IFN-γ Responses to an Insulin Mimotope

Subjects with new-onset T1D (n=28) were recruited from the Barbara Davis Center for Diabetes clinics. Non-diabetic controls (n=27) were healthy adult volunteers negative for all islet autoantibodies. The study protocol was approved by the Institutional Review Board and written informed consent was obtained from all study participants. The T1D subjects had a very short duration of diabetes with the mean time from diagnosis only 15 days; 26/28 (93%) T1D individuals had diabetes less than 3 weeks prior to assays being performed. All subjects were HLA genotyped. Islet autoantibodies to insulin, GAD65, IA-2, and ZnT8 were measured from the serum by radioimmunoassay as previously described (42). HLA-DRB, DQA, and DQB genotyping was performed using linear arrays of immobilized sequence-specific oligonucleotides similar to previously described methodology (43). Demographic and clinical characteristics are summarized in the following table:

TABLE 2

Clinical characteristics, islet autoantibody status, and HLA genotype of study participants

| Characteristic | Type 1 Diabetes (n = 28) | No Diabetes (n = 27) | P-value |
|---|---|---|---|
| Age, years | | | |
| Mean (SD) | 16.1 (7.3) | 27.7 (11.2) | <0.01 |
| Median | 14 | 23 | |
| Range | 10-49 | 14-53 | |
| Gender, Number (%) | | | |
| Male | 19 (68) | 14 (52) | 0.28 |
| Female | 9 (32) | 13 (48) | |
| Diabetes Duration, days | | | |
| Mean (SD) | 15 (22.1) | NA | NA |
| Median | 11 | | |
| Range | 0-114 | | |
| Islet Autoantibody Positive, | | | |
| Number (%) | 25 (89.3) | 0 (0) | NA |
| HLA-DQ Genotype, Number (%) | | | |
| Two alleles with non-β57Asp[A] | 17 (61) | 9 (33) | 0.11 |
| One allele with non-β57Asp | 9 (32) | 14 (52) | |
| No alleles with non-β57Asp | 2 (7) | 4 (15) | |

[A]DQβ*03:02, 02:01, 02:02, 05:01, and 06:04 lack β57 aspartic acid.

The non-diabetic control subjects are slightly older than the T1D patients, and contain more individuals having 'diabetogenic' DQ alleles, which have a polymorphism at position 57 in the β chain (non-β57Asp), than expected in the general population to allow for comparisons between T1D and control subjects. FIG. 1A outlines the study participants and their given DQ genotypes.

Cytokine enzyme-linked immunosorbent spot (ELISPOT) responses from unfractionated peripheral blood mononuclear cells (PBMCs) were measured as previously described using the human IFN-γ and IL10 ELISPOT kits (UCyTech Biosciences) (44). Briefly, freshly isolated PBMCs (1×106) were cultured in 250 μl of serum free AIM-V® Medium (Invitrogen) and 10 μM of peptide which were dissolved in PBS. The cells were supplemented with an additional 250 μl of medium after 24 h, and harvested 24 h later. After washing, the cells were resuspended in 300 μl medium and transferred as three 100 μl aliquots to 96-well clear polystyrene culture plates coated with the appropriate cytokine capture monoclonal antibody and subsequently treated with 1× blocking solution (UCyTech). Seventeen hours later, the cells were removed by decanting, and the wells washed (2×PBS, and 5×PBS containing 0.05% Tween-20). Spots were then formed by sequential incubations with the biotinylated 2nd site anti-IFN-γ or anti-IL10, gold-labeled goat anti-biotin, and a precipitating silver substrate. Spots were enumerated with a Bioreader 4000 Pro X (BIO-SYS GmbH). No antigen wells were a negative control and 1 μl of the Pentacel vaccine (Sanofi Pasteur) was used as a positive control stimulus in each assay.

Total spot numbers from ELISPOT assays were analyzed with a nonparametric Mann-Whitney test (rank sum test). ELISPOT response rates between T1D and controls for a given condition were compared with a two-sided Fisher's exact text. For CFSE proliferation assays, a Wilcoxon signed rank test compared samples from the same subject. For all statistical tests, a two-tailed p value of <0.05 is considered significant. Analyses were performed using GraphPad Prism 4.0 software.

We measured IFN-γ and IL10 ELISPOT responses to the native insulin B:9-23 peptide and two insulin mimotopes (Tables S1 and S2).

TABLE S1

IFN-γ and IL10 ELISPOT responses to insulin peptides by HLA genotype in new onset type 1 diabetes subjects

| | Patient Data | | | HLA DR and DQ Alleles | | | | | | IFN-γ Total ELISPOTS | |
|---|---|---|---|---|---|---|---|---|---|---|---|
| | Age | Sex | T1D | Allele1 | | | Allele2 | | | | |
| Case | (yrs) | | (Days) | DRB1 | DQA1 | DQB1 | DRB1 | DQA2 | DQB2 | No Ag | Pentcel |
| 1 | 12 | M | 8 | 404 | 301 | 302 | 301 | 501 | 201 | 3 | 350 |
| 2 | 13 | M | 114 | 401 | 301 | 302 | 101 | 101 | 501 | 2 | 223 |
| 3 | 14 | M | 12 | 401 | 301 | 302 | 101 | 101 | 501 | 2 | 181 |
| 4 | 20 | M | 15 | 301 | 501 | 201 | 301 | 501 | 201 | 13 | 284 |
| 5* | 14 | M | 9 | 301 | 501 | 201 | 101 | 101 | 501 | 2 | 113 |
| 6 | 16 | M | 12 | 401 | 301 | 302 | 801 | 301 | 302 | 0 | 181 |
| 7 | 19 | M | 6 | 401 | 301 | 302 | 701 | 201 | 202 | 3 | 160 |
| 8 | 14 | M | 14 | 401 | 301 | 302 | 701 | 201 | 202 | 1 | 278 |
| 9 | 14 | M | 11 | 301 | 501 | 201 | 301 | 501 | 201 | 0 | 138 |
| 10 | 14 | M | 60 | 301 | 501 | 201 | 1302 | 102 | 604 | 1 | 87 |
| 11 | 12 | F | 7 | 301 | 501 | 201 | 101 | 101 | 501 | 5 | 168 |
| 12 | 16 | F | 6 | 401 | 301 | 302 | 301 | 501 | 201 | 5 | 370 |
| 13 | 13 | F | 0 | 401 | 301 | 302 | 301 | 501 | 201 | 8 | 300 |
| 14 | 21 | F | 8 | 301 | 501 | 201 | 1302 | 102 | 604 | 0 | 206 |
| 15 | 15 | F | 1 | 301 | 501 | 201 | 1302 | 102 | 604 | 6 | 357 |
| 16 | 15 | M | 14 | 404 | 301 | 302 | 407 | 301 | 302 | 0 | 440 |
| 17 | 14 | M | 9 | 301 | 501 | 201 | 301 | 501 | 201 | 1 | 305 |
| 18 | 27 | M | 0 | 404 | 301 | 302 | 1301 | 103 | 602 | 4 | 283 |
| 19* | 11 | F | 18 | 407 | 301 | 302 | 1406 | 501 | 301 | 4 | 270 |
| 20 | 16 | M | 11 | 301 | 501 | 201 | 404 | 301 | 301 | 0 | 41 |
| 21 | 49 | M | 15 | 401 | 301 | 302 | 801 | 401 | 402 | 3 | 458 |
| 22 | 16 | F | 14 | 701 | 201 | 202 | 401 | 301 | 301 | 2 | 152 |
| 23 | 14 | M | 7 | 405 | 301 | 302 | 801 | 401 | 402 | 2 | 96 |
| 24 | 14 | M | 14 | 101 | 101 | 501 | 1304 | 501 | 301 | 0 | 68 |
| 25 | 12 | M | 12 | 401 | 301 | 302 | 302 | 401 | 402 | 1 | 300 |
| 26 | 10 | F | 0 | 101 | 101 | 501 | 401 | 301 | 301 | 0 | 413 |
| 27* | 15 | M | 12 | 401 | 301 | 301 | 1104 | 501 | 301 | 0 | 128 |
| 28 | 12 | F | 7 | 1602 | 102 | 502 | 1102 | 501 | 301 | 0 | 187 |

| | IFN-γ Total ELISPOTS | | | IL-10 Total ELISPOTS | | | | |
|---|---|---|---|---|---|---|---|---|
| | B: 9-23 | | | | | B: 9-23 | | |
| Case | Wt | B22E | B22E 21G | No Ag | Pentacel | Wt | B22E | B22E 21G |
| 1 | 5 | 26 | 4 | — | — | — | — | — |
| 2 | 3 | 143 | 6 | — | — | — | — | — |
| 3 | 5 | 70 | 6 | — | — | — | — | — |
| 4 | 35 | 151 | 34 | — | — | — | — | — |
| 5* | 1 | 2 | 0 | — | — | — | — | — |
| 6 | 1 | 4 | 1 | — | — | — | — | — |
| 7 | 7 | 6 | 4 | — | — | — | — | — |
| 8 | 0 | 4 | 2 | — | — | — | — | — |
| 9 | 1 | 30 | 1 | — | — | — | — | — |
| 10 | 1 | 6 | 1 | — | — | — | — | — |
| 11 | 6 | 38 | 2 | — | — | — | — | — |
| 12 | 13 | 15 | 7 | — | — | — | 1 | — |
| 13 | 11 | 6 | 4 | 3 | 160 | 1 | 1 | 1 |
| 14 | 154 | 3 | 1 | 1 | 301 | 1 | 70 | 2 |
| 15 | 0 | 6 | 1 | 0 | 545 | 2 | 6 | 1 |
| 16 | 4 | 12 | 0 | 1 | 304 | 0 | 161 | 3 |
| 17 | 1 | 3 | 0 | 1 | 303 | 0 | 7 | 4 |
| 18 | 5 | 163 | 2 | — | — | — | — | — |
| 19* | 4 | 30 | 11 | — | — | — | — | — |
| 20 | 1 | 4 | 0 | — | — | — | — | — |
| 21 | 6 | 19 | 5 | — | — | — | — | — |
| 22 | 1 | 8 | 0 | — | — | — | — | — |
| 23 | 1 | 19 | 10 | — | — | — | — | — |
| 24 | 0 | 4 | 1 | 0 | 88 | 6 | 23 | 3 |
| 25 | 0 | 2 | 1 | 0 | 521 | 1 | 7 | 1 |
| 26 | 1 | 10 | 2 | 2 | 350 | 0 | 1 | 4 |
| 27* | 3 | 27 | 5 | — | — | — | — | — |
| 28 | 4 | 27 | 8 | — | — | — | — | — |

*Denotes islet autoantibody negative subject
Underlined and bold allele contains non-β57Asp

TABLE S2

IFN-γ and IL10 ELISPOT responses to insulin peptides by HLA genotype in control subjects without diabetes

| | Patient Data | | HLA DR and DQ Alleles | | | | | | IFNg Total ELISPOTS | | | | | IL-10 Total ELISPOTS | | | | |
|---|---|---|---|---|---|---|---|---|---|---|---|---|---|---|---|---|---|---|
| | | | Allele1 | | | Allele2 | | | No | Pen- | | B: 9-23 | | No | Pen- | | B: 9-23 | |
| | Age | | | | | | | | | | | | B22E | | | | | B22E |
| Case | (yrs) | Sex | DRB1 | DQA1 | DQB1 | DRB1 | DQA2 | DQB2 | Ag | tcel | Wt | B22E | 21G | Ag | tacel | Wt | B22E | 21G |
| 1 | 21 | M | 404 | 301 | 302 | 101 | 101 | 501 | 4 | 136 | 1 | 34 | 8 | 1 | 88 | 3 | 31 | 15 |
| 2 | 18 | F | 401 | 301 | 201 | 701 | 201 | 202 | 4 | 154 | 4 | 2 | 32 | | High Background | | | |
| 3 | 15 | M | 404 | 301 | 302 | 701 | 201 | 202 | 1 | 135 | 0 | 0 | 1 | 11 | 30 | 6 | 7 | 0 |
| 4 | 14 | F | 404 | 301 | 302 | 301 | 501 | 201 | 0 | 227 | 3 | 1 | 26 | 2 | 35 | 4 | 5 | 23 |
| 5 | 32 | F | 402 | 301 | 302 | 301 | 501 | 201 | 0 | 302 | 1 | 2 | 1 | 4 | 305 | 3 | 13 | 5 |
| 6 | 24 | F | 301 | 501 | 201 | 901 | 301 | 201 | 5 | 300 | 4 | 3 | 5 | 4 | 311 | 120 | 66 | 63 |
| 7 | 29 | F | 102 | 101 | 501 | 1201 | 101 | 501 | 3 | 307 | 8 | 10 | 5 | 3 | 304 | 3 | 11 | 4 |
| 8* | 23 | F | 301 | 501 | 201 | 701 | 201 | 202 | 1 | 304 | 0 | 0 | 0 | 2 | 311 | 0 | 11 | 4 |
| 9 | 22 | M | 301 | 501 | 201 | 101 | 101 | 501 | 1 | 358 | 0 | 9 | 0 | 3 | 330 | 30 | 13 | 5 |
| 10 | 17 | M | 101 | 101 | 501 | 408 | 301 | 301 | 0 | 86 | 2 | 123 | 10 | 4 | 93 | 4 | 115 | 27 |
| 11 | 45 | F | 404 | 301 | 302 | 1101 | 501 | 301 | 3 | 111 | 5 | 86 | 11 | 5 | 27 | 4 | 221 | 43 |
| 12 | 53 | F | 401 | 301 | 302 | 404 | 301 | 301 | 0 | 44 | 0 | 2 | 6 | 2 | 16 | 6 | 44 | 3 |
| 13 | 41 | M | 403 | 301 | 302 | 1501 | 102 | 601 | 2 | 98 | 4 | 12 | 3 | 3 | 49 | 8 | 27 | 16 |
| 14* | 50 | F | 1302 | 102 | 604 | 401 | 301 | 301 | 0 | 13 | 0 | 0 | 0 | 3 | 20 | 7 | 24 | 10 |
| 15* | 53 | M | 404 | 301 | 302 | 1501 | 102 | 602 | 0 | 17 | 1 | 0 | 3 | 2 | 15 | 12 | 52 | 11 |
| 16 | 33 | F | 1302 | 102 | 604 | 801 | 401 | 402 | 0 | 211 | 0 | 2 | 0 | 7 | 164 | 0 | 5 | 1 |
| 17 | 24 | F | 101 | 101 | 501 | 401 | 301 | 301 | 1 | 465 | 0 | 16 | 2 | 4 | 321 | 22 | 17 | 11 |
| 18 | 25 | M | 103 | 101 | 501 | 1501 | 102 | 602 | 0 | 303 | 2 | 39 | 0 | 0 | 281 | 1 | 43 | 0 |
| 19* | 16 | M | 402 | 301 | 202 | 1104 | 501 | 301 | 1 | 314 | 7 | 73 | 5 | 0 | 162 | 7 | 31 | 6 |
| 20 | 23 | M | 701 | 201 | 202 | 901 | 301 | 303 | 0 | 406 | 2 | 89 | 2 | 3 | 322 | 4 | 113 | 7 |
| 21 | 23 | M | 301 | 501 | 201 | 1501 | 102 | 602 | 1 | 326 | 0 | 19 | 4 | 3 | 357 | 1 | 231 | 11 |
| 22 | 22 | F | 101 | 101 | 501 | 1502 | 103 | 601 | 0 | 313 | 0 | 7 | 2 | 1 | 307 | 3 | 108 | 9 |
| 23 | 23 | M | 102 | 101 | 501 | 1501 | 102 | 602 | 0 | 301 | 2 | 25 | 1 | 2 | 303 | 3 | 31 | 5 |
| 24 | 30 | M | 401 | 301 | 301 | 1103 | 501 | 301 | 0 | 304 | 0 | 6 | 0 | 1 | 310 | 11 | 80 | 20 |
| 25 | 23 | F | 1101 | 501 | 301 | 1101 | 501 | 301 | 0 | 300 | 0 | 9 | 1 | 3 | 348 | 7 | 13 | 8 |
| 26 | 26 | M | 1501 | 102 | 602 | 1301 | 103 | 603 | 2 | 304 | 1 | 175 | 1 | 1 | 301 | 1 | 319 | 3 |
| 27 | 23 | M | 1104 | 501 | 301 | 1501 | 102 | 602 | 0 | 314 | 0 | 10 | 0 | 4 | 312 | 1 | 29 | 6 |

*Denotes a first degree relative with T1D
Underlined and bold allele contains non-β57Asp The native amino acid sequence of insulin B chain amino acids 9-23 is listed in FIG. 1B along with two mimotopes designed to bind 'diabetogenic' DQ alleles, mainly DQ8 and DQ2, in an unfavorable binding position or 'register.' A peptide can bind in multiple positions or registers with amino acids occupying positions p1-p9 in the peptide binding groove (18, 19). A peptide is anchored by amino acids binding to distinct structural pockets at position 1, 4, 6, and 9 of the MHC class II peptide binding groove, while the remaining amino acids can interact with a T cell receptor (20, 21). It is well established that subtle structural changes to pocket 9 in the peptide binding groove influence T1D susceptibility in mice and humans. The two mimotopes studied are insulin B:9-23 (B22E) and B:9-23 (B21G, 22E) as the amino acid substitutions allow the mimotopes to be anchored at pocket 9, as B22 arginine of the native peptide is an otherwise unfavorable match (FIG. 1B).

Cytokine ELISPOT results were obtained from all T1D and control subjects based upon DQ genotype with alleles containing β57 aspartic acid. Freshly isolated PBMCs were cultured in the presence or absence of a single insulin peptide for 48 hours, washed, and then cells transferred to an IFN-γ or IL10 monoclonal antibody coated plate for overnight culture followed by development and enumeration of ELISPOTs. We conducted a comparison of individual background (no antigen stimulus) to native insulin B:9-23, B:9-23 (B22E), and B:9-23 (B21G, 22E) IFN-γ responses in T1D and (B) control subjects. There were more robust responses to the B:9-23 (B22E) mimotope in both T1D and controls compared to no antigen and native B:9-23. IL10 responses from T1D and controls were also obtained. IL10 ELISPOTs were only measured in a subset of T1D patients (n=8). Overall, controls made more IL10 to the insulin peptides compared to T1D subjects and have robust IL10 responses to the B:9-23 (B22E) mimotope. The total IFN-γ ELISPOTs from T1D (n=28) and control subjects (n=27) reveal robust responses to the insulin B22E mimotope (B22Arg→Glu) in comparison to background. Furthermore, the responses to the insulin B22E mimotope are much greater than that of native B:9-23 peptide. We also examined the inflammatory responses based upon disease status and HLA-DQ genotype. T1D and controls are grouped by the number of DQ alleles having β57Asp. T1D subjects with two non-B57Asp DQ alleles (mainly DQ8 and DQ2) had more IFN-γ producing T cells to the insulin B22E mimotope compared to HLA matched controls (P=0.02, table 2). In individuals having only one DQ allele with non-β57Asp, there was no difference in IFN-γ ELISPOT responses between T1D and controls for any of the insulin peptides. Among the three insulin peptides, only the B22E mimotope was able to discriminate IFN-γ responses between T1D and control subjects in those having two non-β57Asp DQ alleles. The responses to Pentacel, a childhood vaccine, did not differ between T1D and control subjects (table 3). (Analysis of the data by comparing stimulation index (spot# condition/spot# background) for each peptide does not change the response to the insulin B22E mimotope or alter the statistics).

TABLE 3

Comparison of IFN-γ ELISPOT responses to insulin peptides between T1D and controls based upon DQ Genotype

|  | β57D | T1D mean (SEM) | Control mean (SEM) | P-value |
|---|---|---|---|---|
| B: 9-23 | −/− | 15 (9) | 2 (1) | ns |
|  | +/− | 2 (1) | 2 (1) | ns |
| B: 9-23 (B22E) | −/− | 31 (11) | 7 (4) | 0.02 |
|  | +/− | 29 (17) | 35 (11) | ns |
| B: 9-23 (B21G, 22E) | −/− | 4 (2) | 9 (4) | ns |
|  | +/− | 4 (1) | 4 (1) | ns |
| Pentacel* | −/− | 244 (25) | 247 (29) | ns |
|  | +/− | 231 (50) | 215 (40) | ns |

*Pentacel (positive control) is a childhood vaccine containing immunogens directed against diphtheria, tetanus, pertussis, poliomyelitis, and *Haemophilus influenza* type b.

With the insulin B22E mimotope providing robust IFN-γ responses, we evaluated the persistence of the response over time in a new-onset T1D subject. The B22E mimotope response is reproducible over time with fluctuations in the absolute number of IFN-γ secreting T cells. During this time the subject remained unresponsive to wild type insulin B:9-23 and the B21G, 22E mimotope. A positive response to Pentacel was observed for each ELISPOT assay.

Example 2: Regulatory Responses are Dependent Upon Disease Status and HLA-DQ Genotype In addition to IFN-γ, IL10 responses were also measured in controls (n=26) and a subset of new-onset T1D patients (n=8). Despite producing some IFN-γ to the insulin B22E mimotope, controls had significant IL10 responses, while several T1D subjects did produce IL10 (FIG. 2). Controls had more IL10 producing cells than diabetics when stimulated with native insulin B:9-23 and a trend towards statistical significance with the B22E mimotope (FIG. 3, left). Examining just the control subjects, IL10 producing T cells exist to the insulin B22E mimotope in those subjects having at least one or both DQ alleles with β57Asp (FIG. 3, right). Having this protective polymorphism in the DQ beta chain resulted in 17/18 (94%) controls having greater than 5 IL10 spots compared to just 3/8 (38%) lacking a protective HLA-DQ allele (p=0.005).

To summarize the cytokine ELISPOT results, cytokine responses to the insulin B:9-23 (B22E) mimotope are efficiently detected in new-onset T1D subjects having DQ alleles associated with diabetes while controls respond by dominantly producing IL10 to this peptide when at least one diabetes protective DQ allele is present.

Example 3: Proliferation of CD4 T Cells to the Insulin Peptides

We next examined whether the insulin peptides result in proliferation of CD4 T cells from the peripheral blood of subjects with established T1D selected based upon having two non-β57Asp DQ alleles (Table S3).

TABLE S3

Clinical characteristics and HLA genotype of T1D subjects with proliferation assays

| Case No. | Age (years) | Sex | T1D (years) | DQ Genotype | HLA DR and DQ Alleles | | | | | |
|---|---|---|---|---|---|---|---|---|---|---|
|  |  |  |  |  | DRB1 | DQA1 | DQB1 | DRB2 | DQA2 | DQB2 |
| 1* | 30 | F | 29 | 2/8 | 0301 | 0501 | 0201 | 0405 | 0301 | 0302 |
| 2* | 32 | F | 6 | 2/8 | 0301 | 0501 | 0201 | 0401 | 0301 | 0302 |
| 3 | 57 | F | 20 | 2/2 | 0301 | 0501 | 0201 | 0301 | 0501 | 0201 |
| 4* | 33 | M | 20 | 2/8 | 0301 | 0501 | 0201 | 0401 | 0301 | 0302 |
| 5 | 23 | F | 17 | 8/8 | 0401 | 0301 | 0302 | 0401 | 0301 | 0302 |
| 6 | 28 | M | 1.5 | 2/8 | 0301 | 0501 | 0201 | 0401 | 0301 | 0302 |
| 7 | 28 | M | 20 | 2/8 | 0301 | 0501 | 0201 | 0401 | 0301 | 0302 |

*T cell receptor Vα gene sequencing performed

PBMCs were isolated from whole blood using Ficoll-paque and resuspended at a density of 106/ml in CFSE labeling buffer (1% BSA in PBS). Cells were labeled with 1 µM CFSE (eBioscience) for 10 minutes at 37° C. Labeling was quenched by adding chilled media (IM DM supplemented with 5% heat inactivated human AB serum, 100 µg/ml Pen-Strep, 100 µM MEM NEAA, and 50 µM 2-mercaptoethanol) at 5 times the volume at 0° C.; cells were then incubated on ice for 5 minutes. Labeled cells were washed in PBS with 1% human AB serum, resuspended in media, and plated into a 24-well tissue culture plate at 106 cells/well in 1 ml of media. Peptides (Genemed Synthesis Inc.) were HPLC purified (>95%), dissolved in PBS at a neutral pH, and used at a concentration of 10 µM·DQ antibody (SPV-L3, Abcam) was added at defined concentrations, and Pentacel vaccine (Sanofi Pasteur) was added at 2 µl per well. After seven days of incubation at 37° C. in 5% CO2, non-adherent cells were harvested and stained for FACS analysis using antibodies to CD4 (RPA-T4, BD Bioscience) and CD8 (RPA-T8, BD Bioscience). FACS analysis was done using a Becton-Dickenson FACS Caliber and cell sorting for CD4+CFSElo cells was done with a Beckman Coulter Moflo XDP 100.

FIGS. 4A-4E show the proliferation results after bulk unfractionated PBMCs were labeled with CFSE and cultured for 7 days in the presence of insulin peptides without the addition of any in vitro stimulus, i.e. no IL-2, anti-CD3, or anti-CD28. Similar to the IFN-γ ELISPOT assays, the B22E mimotope resulted in proliferation of CD4 T cells much more than the wild type peptide. Of the tested subjects, all of them had a distinct T cell population proliferating in response to the insulin B22E mimotope more than background and wild type B:9-23 (FIG. 4B, C). To determine whether these proliferative responses are DQ restricted, a DQ blocking antibody was added to the culture during proliferation. The antibody is able to block the proliferative response to the mimotope in a dose dependent fashion (FIG. 4D). The DQ antibody doses not block the proliferation of a DR restricted tetanus toxin response, nor does an isotype antibody reduce proliferation (data not shown). All of the tested T1D subjects had less CD4+CFSE$^{lo}$ cells following proliferation to the insulin B22E mimotope in the presence of the DQ antibody, indicating the T cell response to the peptide is DQ restricted (FIG. 4E).

Example 4: T Cell Receptor V Alpha Gene Usage after Proliferation to an Insulin Peptide With the ability to proliferate CD4 T cells to the insulin B22E mimotope, we examined whether there is skewing of the T cell receptor variable (V) genes in CD4+CFSE$^{lo}$ cells. In the NOD mouse, it is well established that there is V alpha gene skewing from islet infiltrating CD4 T cells responding to insulin with several dominant V alpha genes used to recognize the insulin B:9-23 peptide (22, 23).

Three individuals had TCR α-chain sequencing performed on sorted CD4 T cells before peptide proliferation and then on CD4+CFSElo cells after one week of proliferation. Total RNA was directly extracted from sorted cells using the RNeasy Mini kit (Qiagen) for cells before proliferation and the PicoPure RNA isolation kit (Life Technologies) for those after proliferation. Single-strand cDNA ligated with the universal oligonucleotide sequence at the 5' end was synthesized using the Clontech SMARTer™ RACE cDNA Amplification Kit according to the manufacturer's instructions. To amplify TCR-α and TCR-β chains, a two-step PCR was performed. PCR reactions were generated for α- and β-chains separately using the Universal Primer A Mix supplied from the SMARTer RACE cDNA Amplification Kit along with a primer designed on the constant region of α-(CCAGGCCACAGCACTGTTGCTCTTGAAGTCC (SEQ ID NO:22)) and β-chains (GCTGACCCCACTGTG-CACCTCCTTCCC (SEQ ID NO:23)), respectively. The first PCR products were further amplified with nested primers ligated with the 454 adaptor sequences containing a multiple identifier sequence: forward primer for both α- and β-chains (CCTATCCCCTGTGTGCCTTGGCAGTCTCA-GAAGCAGTGGTATCAACGCAGAGT (SEQ ID NO:24)), reverse primer for α-chains (CCATCTCATCCCTGCGT-GTCTCCGACTCAG (SEQ ID NO:25)—multiple identifier sequence—GCTGGTACACGGCAGGGTCAGGGT (SEQ ID NO:26), and reverse primer for β-chains (CCATCT-CATCCCTGCGTGTCTCCGACTCAG (SEQ ID NO:25)—multiple identifier sequence—CACAGCGAC-CTCGGGTGGGAACAC (SEQ ID NO:27).

These PCR products were agarose gel-purified followed by further purification with the AMPure XP Beads (Beckman Coulter), subject to emulsion PCR with the 454 GSJR titanium chemistry, and sequenced on the 454 GSJR instrument (Roche). All sequences obtained from 454 sequencing were analyzed by the IMGT-HighV-QUEST algorithm (45) to identify Vgene, Jgene, and junction sequences, followed by additional analysis by in-house software to determine frequencies of Vgene usages by individual TCR sequences. Vgene frequencies determined by mean values from the 12 PCR reactions were analyzed for individual samples. Alignment cluster analysis was further performed using the Clustal-Omega algorithm.

In three HLA matched T1D subjects, all having two non-β57Asp DQ alleles, sorted CD4+ T cells were analyzed for V gene usage of TCR alpha chains before and after proliferation to the insulin B22E mimotope. There is skewing with several V alpha genes and one V delta gene, located within the T cell receptor alpha locus on chromosome 14, used more and less predominantly compared to baseline in all three subjects (FIG. 5A). Analyzing phylogenetic trees of Vgene sequences indicates that four of the prevalently used V genes (T cell receptor alpha variable [TRAV] 38-1, TRAV 38-2, TRAV 19, and T cell receptor delta variable [TRDV] 1) cluster together based upon similarity in CDR1 and CDR2 sequences (FIGS. 5B, 5C). The V alpha gene skewing and clustering of dominantly used genes based upon CDR1 and CDR2 regions are consistent with antigen specific T cell proliferation.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

REFERENCES

1. Atkinson M A, Eisenbarth G S, & Michels A W (2014) Lancet 383(9911):69-82.

2. Harjutsalo V, Sjoberg L, & Tuomilehto J (2008) *Lancet.* 371(9626):1777-1782.
3. Patterson C C, Dahlquist G G, Gyurus E, Green A, & Soltesz G (2009) *Lancet* 373(9680):2027-2033.
4. Ziegler A G et al. (2013) *JAMA* 309(23):2473-2479.
5. Skyler J S et al. (2002) 346(22):1685-1691.
6. Skyler J S et al. (2005) *Diabetes Care* 28(5):1068-1076.
7. Nanto-Salonen K et al. (2008) *Lancet* 372(9651):1746-1755.
8. Alleva D G et al. (2001) *J. Clin. Invest* 107(2):173-180.
9. Nakayama M et al. (2005) *Nature* 435(7039):220-223.
10. Nakayama M et al. (2007) *J. Clin. Invest.* 117(7):1835-1843.
11. Stadinski B D et al. (2010) *Proc. Natl. Acad. Sci. U.S.A* 107(24):10978-10983.
12. Crawford F et al. (2011) *Proc. Natl. Acad. Sci. U.S.A* 108(40):16729-16734.
13. Daniel C, Weigmann B, Bronson R, & von B H (2011) *J. Exp. Med* 208(7):1501-1510.
14. Erlich H et al. (2008) *Diabetes.* 57(4):1084-1092.
15. Concannon P, Rich S S, & Nepom G T (2009) *N. Engl. J. Med.* 360(16):1646-1654.
16. Barrett J C et al. (2009) *Nat. Genet.* 41(6):703-707.
17. Jones E Y, Fugger L, Strominger J L, & Siebold C (2006) *Nature Reviews Immunology* 6(4):271-282.
18. Latek R R et al. (2000) *Immunity.* 12(6):699-710.
19. Corper A L et al. (2000) *Science* 288(5465):505-511.
20. Lee K H, Wucherpfennig K W, & Wiley D C (2001) *Nature Immunology* 2(6):501-507.
21. McFarland B J & Beeson C (2002) *Med. Res. Rev.* 22(2):168-203.
22. Simone E et al. (1997) *Proc Natl Acad Sci USA* 94(6):2518-2521.
23. Nakayama M et al. (2012) *Diabetes.* 61(4):857-865.
24. Roep B O, Buckner J, Sawcer S, Toes R, & Zipp F (2012) *Nat. Med.* 18(1):48-53.
25. Mannering S I et al. (2010) *Clin. Exp. Immunol.* 162(2):197-209.
26. Herold K C et al. (2009) *Diabetes* 58(11):2588-2595.
27. Tiittanen M, Huupponen J T, Knip M, & Vaarala O (2006) *Diabetes* 55(12):3446-3454.
28. Fuchtenbusch M, Kredel K, Bonifacio E, Schnell O, & Ziegler A G (2000) *Diabetes* 49(6):918-925.
29. Ettinger R A, Liu A W, Nepom G T, & Kwok V W V (2000) *J. Immunol.* 165(6):3232-3238.
30. Kwok V W V, Domeier M E, Johnson M L, Nepom G T, & Koelle D M (1996) *J Exp. Med* 183(3):1253-1258.
31. Fousteri G et al. (2012) *Diabetes.* 61(5):1169-1179.
32. Hallmayer J et al. (2009) *Nat. Genet.* 41(6):708-711.
33. Barker J M & Liu E (2008) *Adv. Pediatr.* 55:349-365.
34. Bukhari W, Barnett M H, Prain K, & Broadley S A (2012) *Int. J. Mol. Sci.* 13(10):12970-12993.
35. Schmidt H, Williamson D, & Ashley-Koch A (2007) *American Journal of Epidemiology* 165(10):1097-1109.
36. Nepom G T & Kwok V W V (1998) *Diabetes* 47(8):1177-1184.
37. Schubert D A et al. (2012) *J. Exp. Med.* 209(2):335-352.
38. Danke N A, Koelle D M, Yee C, Beheray S, & Kwok V W V (2004) *J Immunol* 172(10):5967-5972.
39. Arif S et al. (2004) *J. Clin. Invest* 113(3):451-463.
40. Skyler J S (2013) *Diabet. Med.* 30(2):161-169.
41. Steck A K, Armstrong T K, Babu S R, & Eisenbarth G S (2011) *Diabetes.* 60(3):1045-1049.
42. Yu L et al. (1996) *J Clin Endocrinol Metab* 81(12):4264-4267.
43. Bugawan T L & Erlich H A (1991) *Immunogenetics* 33(3):163-170.
44. Nagata M et al. (2004) *Ann. N. Y. Acad. Sci.* 1037:10-15.
45. Alamyar E, Giudicelli V, Li S, Duroux P, & Lefranc M P (2012) *Immunome. Res.* 8(1):26.

What is claimed is:

1. A method for assessing the efficacy of a therapeutic or preventative therapy in a human subject with T1D, or suspected of having T1D, or at risk of developing T1D, comprising:
    contacting peripheral blood mononuclear cells (PBMC) from a first biological sample from a subject with a peptide comprising the amino acid sequence of SEQ ID NO:2 and detecting IFN-gamma and IL10 cytokine production by the PBMC by enzyme-linked immunospot (ELISPOT) assay;
    contacting PBMC from a second biological sample taken from the subject after a period of treatment with the therapy, with a peptide comprising the amino acid sequence of SEQ ID NO:2 and detecting IFN-gamma and IL10 cytokine production by the PBMC by enzyme-linked immunospot (ELISPOT) assay;
    assessing the therapy as effective when IFN-gamma cytokine production in the second sample is less than the IFN-gamma cytokine production in the first sample; and,
    assessing the therapy as effective when IL10 cytokine production in the second sample is greater than the IFN-gamma cytokine production in the first sample.

2. The method of claim 1, wherein the therapy is assessed as effective when the ratio of IFN-gamma cytokine to IL10 cytokine (IFN-gamma/IL10) production by the PBMC in the second sample from the subject is greater than the IFN-gamma/IL10 ratio in the first sample from the subject.

3. The method of claim 1, further comprising detecting the proliferation of FoxP3+ regulatory PBMC in the first and the second biological samples from the subject and comparing the proliferation in the regulatory PBMC from the second sample to the first sample.

4. The method of claim 1, wherein the therapy comprises administration of a therapeutically effective amount of a peptide selected from SEQ ID NOs:2-21.

5. The method of claim 1, wherein the first biological sample and the second biological sample comprise isolated CD4+CD25+ PBMC.

* * * * *

UNITED STATES PATENT AND TRADEMARK OFFICE
CERTIFICATE OF CORRECTION

PATENT NO. : 10,363,288 B2
APPLICATION NO. : 15/541074
DATED : July 30, 2019
INVENTOR(S) : Aaron Michels, John Kappler and A. Gottlieb Page 1 of 1

It is certified that error appears in the above-identified patent and that said Letters Patent is hereby corrected as shown below:

On the Title Page

Item [56], Please add the following to the list of OTHER PUBLICATIONS:
U.S. Appl. No. 16/357,397, filed March 19, 2019, Orndorff et al.

Signed and Sealed this
Seventeenth Day of September, 2019

Andrei Iancu
*Director of the United States Patent and Trademark Office*

```
                          SEQUENCE LISTING

<160> NUMBER OF SEQ ID NOS: 39

<210> SEQ ID NO 1
<211> LENGTH: 15
<212> TYPE: PRT
<213> ORGANISM: Homo sapiens

<400> SEQUENCE: 1

Ser His Leu Val Glu Ala Leu Tyr Leu Val Cys Gly Glu Arg Gly
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 2

Ser His Leu Val Glu Ala Leu Tyr Leu Val Cys Gly Glu Glu Gly
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic Peptide
```

```
<400> SEQUENCE: 3

Ser His Leu Val Glu Ala Leu Tyr Leu Val Cys Gly Gly Glu Gly
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 4

Ser His Leu Val Glu Glu Leu Tyr Leu Val Cys Gly Glu Glu Gly
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 5

Ser His Leu Val Glu Glu Leu Tyr Leu Val Cys Gly Glu Arg Gly
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 6

Ser His Leu Val Gly Glu Leu Tyr Leu Val Cys Gly Glu Arg Gly
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 7

Ser His Leu Val Gly Glu Leu Tyr Leu Val Cys Gly Gly Glu Gly
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 8

Ser His Leu Val Gly Ala Leu Tyr Leu Val Cys Gly Gly Glu Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 9
```

Ser His Leu Val Gly Glu Leu Tyr Leu Val Cys Gly Gly Arg Gly
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 10

Ser His Leu Val Glu Ala Leu Tyr Leu Val Ala Gly Glu Glu Gly
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 11

Ser His Leu Val Glu Ala Leu Tyr Leu Val Ala Gly Gly Glu Gly
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 12

Ser His Leu Val Glu Ala Leu Tyr Leu Val Ala Gly Ala Glu Gly
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 13

Ser His Leu Val Glu Ala Leu Tyr Leu Val Ala Gly Val Glu Gly
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 14

Ser His Leu Val Glu Ala Leu Tyr Leu Val Ala Gly Leu Glu Gly
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 15

Ser His Leu Val Glu Ala Leu Tyr Leu Val Ala Glu Ala Glu Gly
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 16

Ser His Leu Val Glu Ala Leu Tyr Leu Val Ala Ala Glu Asp Gly
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 17

Ser His Leu Val Glu Ala Leu Tyr Leu Val Ala Gln Val Glu Gly
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 18

Ser His Leu Val Glu Ala Leu Tyr Leu Val Ala Ala Leu Glu Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 19

Ser His Leu Val Glu Ala Leu Tyr Leu Val Glu Ala Glu Asp Gly
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 20

Ser His Leu Val Glu Ala Leu Tyr Leu Val Gly Gln Val Glu Gly
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 21

Ser His Leu Val Glu Ala Leu Tyr Leu Val Leu Ala Leu Glu Gly

<210> SEQ ID NO 22
<211> LENGTH: 31
<212> TYPE: DNA
<213> ORGANISM: Artificial Sequence
<220> FEATURE:
<223> OTHER INFORMATION: Synthetic Primer

<400> SEQUENCE: 22
ccaggccaca gcactgttgc tcttgaagtc c                           31

<210> SEQ ID NO 23
<211> LENGTH: 27
<212> TYPE: DNA
<213> ORGANISM: Artificial Sequence
<220> FEATURE:
<223> OTHER INFORMATION: Synthetic Primer

<400> SEQUENCE: 23
gctgacccca ctgtgcacct ccttccc                                27

<210> SEQ ID NO 24
<211> LENGTH: 53
<212> TYPE: DNA
<213> ORGANISM: Artificial Sequence
<220> FEATURE:
<223> OTHER INFORMATION: Synthetic Primer

<400> SEQUENCE: 24
cctatcccct gtgtgccttg gcagtctcag aagcagtggt atcaacgcag agt   53

<210> SEQ ID NO 25
<211> LENGTH: 30
<212> TYPE: DNA
<213> ORGANISM: Artificial Sequence
<220> FEATURE:
<223> OTHER INFORMATION: Synthetic Primer

<400> SEQUENCE: 25
ccatctcatc cctgcgtgtc tccgactcag                             30

<210> SEQ ID NO 26
<211> LENGTH: 24
<212> TYPE: DNA
<213> ORGANISM: Artificial Sequence
<220> FEATURE:
<223> OTHER INFORMATION: Synthetic Primer

<400> SEQUENCE: 26
gctggtacac ggcagggtca gggt                                   24

<210> SEQ ID NO 27
<211> LENGTH: 24
<212> TYPE: DNA
<213> ORGANISM: Artificial Sequence
<220> FEATURE:
<223> OTHER INFORMATION: Synthetic Primer

<400> SEQUENCE: 27
cacagcgacc tcgggtggga acac                                   24

<210> SEQ ID NO 28
<211> LENGTH: 13
<212> TYPE: PRT
<213> ORGANISM: Homo sapiens

<400> SEQUENCE: 28

Thr Tyr Asp Thr Ser Glu Ser Asp Tyr Tyr Leu Phe Trp
1               5                   10

<210> SEQ ID NO 29
<211> LENGTH: 13
<212> TYPE: PRT
<213> ORGANISM: Homo sapiens

<400> SEQUENCE: 29

Thr Tyr Asp Thr Ser Glu Asn Asn Tyr Tyr Leu Phe Trp
1               5                   10

<210> SEQ ID NO 30
<211> LENGTH: 13
<212> TYPE: PRT
<213> ORGANISM: Homo sapiens

<400> SEQUENCE: 30

Thr Tyr Asp Thr Ser Asp Pro Ser Tyr Gly Leu Phe Trp
1               5                   10

<210> SEQ ID NO 31
<211> LENGTH: 13
<212> TYPE: PRT
<213> ORGANISM: Homo sapiens

<400> SEQUENCE: 31

Val Tyr Glu Thr Arg Asp Thr Thr Tyr Tyr Leu Phe Trp
1               5                   10

<210> SEQ ID NO 32
<211> LENGTH: 14
<212> TYPE: PRT
<213> ORGANISM: Homo sapiens

<400> SEQUENCE: 32

Ser Met Lys Gly Glu Ala Ile Gly Asn Tyr Tyr Ile Asn Trp
1               5                   10

<210> SEQ ID NO 33
<211> LENGTH: 13
<212> TYPE: PRT
<213> ORGANISM: Homo sapiens

<400> SEQUENCE: 33

Leu Tyr Glu Thr Ser Trp Trp Ser Tyr Tyr Ile Phe Trp
1               5                   10

<210> SEQ ID NO 34
<211> LENGTH: 14
<212> TYPE: PRT
<213> ORGANISM: Homo sapiens

<400> SEQUENCE: 34

Leu Ile Arg Arg Asn Ser Phe Asp Glu Gln Asn Glu Ile Ser
1               5                   10

<210> SEQ ID NO 35
<211> LENGTH: 14
<212> TYPE: PRT
<213> ORGANISM: Homo sapiens

<400> SEQUENCE: 35

```
Val Ile Arg Gln Glu Ala Tyr Lys Gln Gln Asn Ala Thr Glu
1               5                   10

<210> SEQ ID NO 36
<211> LENGTH: 14
<212> TYPE: PRT
<213> ORGANISM: Homo sapiens

<400> SEQUENCE: 36

Val Ile Arg Gln Glu Ala Tyr Lys Gln Gln Asn Ala Thr Glu
1               5                   10

<210> SEQ ID NO 37
<211> LENGTH: 14
<212> TYPE: PRT
<213> ORGANISM: Homo sapiens

<400> SEQUENCE: 37

Leu Ile Tyr Gln Gly Ser Tyr Asp Gln Gln Asn Ala Thr Glu
1               5                   10

<210> SEQ ID NO 38
<211> LENGTH: 9
<212> TYPE: PRT
<213> ORGANISM: Homo sapiens

<400> SEQUENCE: 38

Leu Ile Arg Gln Gly Ser Asp Glu Gln
1               5

<210> SEQ ID NO 39
<211> LENGTH: 10
<212> TYPE: PRT
<213> ORGANISM: Homo sapiens

<400> SEQUENCE: 39

Leu Leu Arg His Ile Ser Arg Glu Ser Ile
1               5                   10
```